US009763928B2

(12) United States Patent
Duggins et al.

(10) Patent No.: US 9,763,928 B2
(45) Date of Patent: Sep. 19, 2017

(54) MULTI-LAYER NICOTINE-CONTAINING PHARMACEUTICAL COMPOSITION

(75) Inventors: Donna Walker Duggins, Winston-Salem, NC (US); John-Paul Mua, Advance, NC (US); Darrell Eugene Holton, Jr., Clemmons, NC (US); Daniel Verdin Cantrell, Lewisville, NC (US)

(73) Assignee: Niconovum USA, Inc., Winston-Salem, NC (US)

( * ) Notice: Subject to any disclaimer, the term of this patent is extended or adjusted under 35 U.S.C. 154(b) by 366 days.

(21) Appl. No.: 13/370,505

(22) Filed: Feb. 10, 2012

(65) Prior Publication Data
US 2013/0209540 A1    Aug. 15, 2013

(51) Int. Cl.
*A61K 9/00* (2006.01)
*A61K 31/465* (2006.01)
*A61K 9/24* (2006.01)
*A61K 9/28* (2006.01)

(52) U.S. Cl.
CPC .......... *A61K 31/465* (2013.01); *A61K 9/0056* (2013.01); *A61K 9/209* (2013.01); *A61K 9/2886* (2013.01)

(58) Field of Classification Search
CPC .... A61K 31/465; A61K 9/0056; A61K 9/209; A61K 9/2886
See application file for complete search history.

(56) References Cited

U.S. PATENT DOCUMENTS

| | | | |
|---|---|---|---|
| 3,114,642 A | 12/1963 | Meisel | |
| 3,438,787 A | 4/1969 | Du Ross | |
| 3,738,845 A | 6/1973 | Liebrand | |
| 4,452,825 A | 6/1984 | Klacik et al. | |
| 4,806,356 A | 2/1989 | Shaw | |
| 4,967,773 A | 11/1990 | Shaw | |
| 5,098,730 A | 3/1992 | Pepper et al. | |
| 5,110,605 A | 5/1992 | Acharya | |
| 5,314,701 A | 5/1994 | Mentink et al. | |
| 5,362,496 A | 11/1994 | Baker et al. | |
| 5,512,306 A | 4/1996 | Carlsson et al. | |
| 5,525,351 A * | 6/1996 | Dam | 424/440 |
| 5,549,906 A | 8/1996 | Santus | |
| 5,593,684 A | 1/1997 | Baker et al. | |
| 5,629,042 A | 5/1997 | Serpelloni et al. | |
| 5,656,284 A | 8/1997 | Balkin | |
| 5,711,961 A | 1/1998 | Reiner et al. | |
| 5,733,574 A * | 3/1998 | Dam | 424/464 |
| 5,811,126 A | 9/1998 | Krishnamurthy | |
| 5,840,334 A | 11/1998 | Raiden et al. | |
| 5,869,098 A | 2/1999 | Misra et al. | |
| 5,939,100 A | 8/1999 | Albrechtsen et al. | |
| 6,024,981 A | 2/2000 | Khankari et al. | |
| 6,083,531 A | 7/2000 | Humbert-Droz et al. | |
| 6,090,401 A | 7/2000 | Gowan, Jr. et al. | |
| 6,110,495 A * | 8/2000 | Dam | 424/464 |
| 6,183,775 B1 | 2/2001 | Ventouras | |
| 6,221,392 B1 | 4/2001 | Khankari et al. | |
| 6,248,760 B1 | 6/2001 | Wilhelmsen | |
| 6,264,981 B1 | 7/2001 | Zhang et al. | |
| 6,280,761 B1 | 8/2001 | Santus | |
| 6,569,463 B2 | 5/2003 | Patel et al. | |
| 6,583,160 B2 | 6/2003 | Smith et al. | |
| 6,585,997 B2 | 7/2003 | Moro et al. | |
| 6,586,449 B1 | 7/2003 | Walling | |
| 6,676,959 B1 | 1/2004 | Andersson et al. | |
| 6,828,336 B2 | 12/2004 | Walling | |
| 6,849,286 B1 | 2/2005 | Bayerköhler et al. | |
| 6,872,405 B2 | 3/2005 | Takaishi et al. | |
| 6,890,559 B1 | 5/2005 | Bayerköhler et al. | |
| 6,893,654 B2 | 5/2005 | Pinney et al. | |
| 7,025,983 B2 | 4/2006 | Leung et al. | |
| 7,122,198 B1 | 10/2006 | Singh et al. | |
| 7,163,705 B2 | 1/2007 | Johnson et al. | |
| 7,935,362 B2 | 5/2011 | Ream et al. | |
| 8,501,164 B2 | 8/2013 | Chen | |
| 8,545,870 B2 | 10/2013 | Dupinay et al. | |
| 2001/0016593 A1 | 8/2001 | Wilhelmsen | |
| 2003/0176467 A1 | 9/2003 | Andersson et al. | |
| 2003/0215553 A1 | 11/2003 | Ribadeau-Dumas et al. | |
| 2003/0235617 A1 | 12/2003 | Martino et al. | |
| 2004/0052851 A1 | 3/2004 | Graff et al. | |
| 2004/0076665 A1 | 4/2004 | Graff et al. | |
| 2004/0096501 A1 | 5/2004 | Vaya et al. | |
| 2004/0101543 A1 | 5/2004 | Liu et al. | |
| 2004/0191322 A1 * | 9/2004 | Hansson | 424/489 |
| 2004/0253307 A1 | 12/2004 | Hague et al. | |
| 2005/0053665 A1 | 3/2005 | Ek et al. | |
| 2005/0123502 A1 | 6/2005 | Chan et al. | |
| 2005/0214229 A1 | 9/2005 | Pinney et al. | |
| 2006/0171969 A1 | 8/2006 | Macelloni et al. | |
| 2006/0171994 A1 | 8/2006 | Dupinay et al. | |
| 2006/0191548 A1 | 8/2006 | Strickland et al. | |
| 2007/0081949 A1 * | 4/2007 | Dam et al. | 424/48 |
| 2007/0269386 A1 * | 11/2007 | Steen et al. | 424/48 |
| 2007/0269492 A1 | 11/2007 | Steen et al. | |
| 2008/0014302 A1 * | 1/2008 | Elejalde et al. | 426/5 |
| 2008/0038209 A1 | 2/2008 | Andersen | |
| 2008/0063748 A1 * | 3/2008 | Massey et al. | 426/6 |
| 2008/0260807 A1 | 10/2008 | Sharp et al. | |
| 2008/0286340 A1 * | 11/2008 | Andersson et al. | 424/440 |
| 2008/0286341 A1 | 11/2008 | Andersson et al. | |
| 2009/0004248 A1 | 1/2009 | Bunick et al. | |
| 2009/0014018 A1 | 1/2009 | Sengupta et al. | |
| 2009/0023819 A1 | 1/2009 | Axelsson | |
| 2009/0028998 A1 * | 1/2009 | Elejalde et al. | 426/5 |

(Continued)

FOREIGN PATENT DOCUMENTS

EP        2 233 134       9/2010
KR     2010 0117950     11/2010

(Continued)

*Primary Examiner* — Robert A Wax
*Assistant Examiner* — Olga V Tcherkasskaya
(74) *Attorney, Agent, or Firm* — Womble Carlyle Sandridge & Rice, LLP

(57) ABSTRACT

The invention provides a multi-layered pharmaceutical composition comprising two or more formulations with varying properties. In some embodiments, the pharmaceutical compositions provide combinations of different organoleptic properties within the same product. In certain embodiment, these combinations allow for a modified release profile of active ingredients as the user enjoys the pharmaceutical composition. The invention further provides methods for making and using the pharmaceutical composition.

19 Claims, No Drawings

(56) References Cited

U.S. PATENT DOCUMENTS

| | | |
|---|---|---|
| 2009/0092573 A1 | 4/2009 | Andersen |
| 2009/0202635 A1* | 8/2009 | Scott ............................. 424/468 |
| 2009/0263544 A1 | 10/2009 | Soldani |
| 2009/0293889 A1 | 12/2009 | Kumar et al. |
| 2010/0004294 A1 | 1/2010 | Axelsson et al. |
| 2010/0061940 A1 | 3/2010 | Axelsson et al. |
| 2010/0063110 A1 | 3/2010 | Meyer et al. |
| 2010/0124560 A1* | 5/2010 | Hugerth et al. ............. 424/401 |
| 2010/0247586 A1* | 9/2010 | Hugerth et al. ............. 424/401 |
| 2010/0291245 A1 | 11/2010 | Gao et al. |
| 2010/0300463 A1 | 12/2010 | Chen et al. |
| 2011/0139164 A1 | 6/2011 | Mua et al. |
| 2011/0200670 A1 | 8/2011 | Thakkar |
| 2011/0220130 A1 | 9/2011 | Mua et al. |
| 2011/0268809 A1 | 11/2011 | Brinkley et al. |
| 2011/0274628 A1 | 11/2011 | Borschke |
| 2011/0318411 A1* | 12/2011 | Luber et al. ................. 424/464 |
| 2012/0118310 A1 | 5/2012 | Cantrell et al. |
| 2012/0138073 A1 | 6/2012 | Cantrell et al. |
| 2012/0138074 A1 | 6/2012 | Cantrell et al. |
| 2012/0244104 A1 | 9/2012 | Mehta et al. |
| 2013/0071516 A1* | 3/2013 | Elejalde ................... A23G 3/54 426/5 |
| 2013/0074855 A1 | 3/2013 | Holton, Jr. |
| 2013/0078307 A1* | 3/2013 | Holton et al. ................. 424/490 |
| 2013/0098377 A1* | 4/2013 | Borschke et al. ............. 131/270 |
| 2013/0274296 A1* | 10/2013 | Jackson ............... A23G 3/0014 514/343 |

FOREIGN PATENT DOCUMENTS

| | | |
|---|---|---|
| WO | WO 2005/023226 | 3/2005 |
| WO | WO 2006/114604 A2 | 11/2006 |
| WO | WO 2007/104574 | 9/2007 |
| WO | WO 2008/112124 A2 | 9/2008 |
| WO | WO 2008/140372 A1 | 11/2008 |
| WO | WO 2009/037319 | 3/2009 |
| WO | WO 2010/044736 | 4/2010 |

* cited by examiner

MULTI-LAYER NICOTINE-CONTAINING PHARMACEUTICAL COMPOSITION

FIELD OF THE INVENTION

The present invention relates to compositions that contain nicotine, and in particular, to nicotine-containing pharmaceutical compositions intended to be administered to provide a pharmacological effect, or otherwise used for therapeutic purposes.

BACKGROUND OF THE INVENTION

Central nervous system (CNS) conditions, diseases, or disorders can be drug induced; can be attributed to genetic predisposition, infection or trauma; or can be of unknown etiology. They comprise neuropsychiatric disorders, neurological diseases and mental illnesses; and include neurodegenerative diseases, behavioral disorders, cognitive disorders and cognitive affective disorders. The clinical manifestations of several CNS conditions, diseases or disorders have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors).

Nicotinic compounds, such as nicotine, are capable of affecting nicotinic acetylcholinergic receptors (nAChRs). Subtypes of nAChRs exist in both the CNS and the peripheral nervous system (PNS), but the distribution of subtypes is heterogeneous. For instance, certain subtypes which are predominant in vertebrate brain, others predominate at the autonomic ganglia, and others predominate at neuromuscular junction. Activation of nAChRs by nicotinic compounds results in neurotransmitter release. See, for example, Dwoskin et al., *Exp. Opin. Ther. Patents*, 10: 1561-1581 (2000); Schmitt et al., *Annual Reports in Med. Chem.* 35: 41-51 (2000); Huang et al., *J. Am. Chem. Soc.*, 127: 14401-14414 (2006); Arneric et al., *Biochem. Pharmacol.*, 74: 1092-1101 (2007) and Millar, *Biochem. Pharmacol.*, 78: 766-776 (2009); which are incorporated herein by reference.

It has been suggested that administration of nicotine, and other nicotinic compounds, can result in various pharmacological effects. See, for example, U.S. Pat. No. 5,583,140 to Bencherif et al.; U.S. Pat. No. 5,723,477 to McDonald et al.; U.S Pat. No. 7,001,900 to Jacobsen et al.; U.S. Pat. No. 7,135,484 to Dart et al. and U.S. Pat. No. 7,214,686 to Bencherif et al.; and US Pat. Pub. No. 2010/0004451 to Ahmad et al.; which are incorporated herein by reference. As a result, it has been suggested that nicotine, and other nicotinic compounds, can exhibit utility in the treatment of a wide variety of conditions, diseases, and disorders, including those that affect the CNS. Additionally, administration of nicotine and nicotinic compounds has been proposed for treatment of certain other conditions, diseases, and disorders. See, for example, U.S. Pat. No. 5,604,231 to Smith et al.; U.S. Pat. No. 5,811,442 to Bencherif et al.; U.S. Pat. No. 6,238,689 to Rhodes et al.; and U.S. Pat. No. 6,489,349 to Bencherif et al.; which are incorporated herein by reference. Furthermore, administration of nicotine has been employed in an effort to help cigarette smokers quit smoking (i.e., as a smoking cessation aid). For example, nicotine has been an active ingredient of various types of so-called "nicotine replacement therapy" or "NRT" products. See, for example, background art discussed in U.S. patent application Ser. No. 13/278,877 to Borschke et al, filed Oct. 21, 2011, which are incorporated by reference herein.

One particular method that has been employed to provide oral administration of nicotine is through the use of nicotine-containing lozenge or tablet types of products.

Nicotine-containing lozenge, tablet, and microtab types of products have been marketed, for example, under the tradenames "Commit®," "Nicorette®," "Nicotinell®" and "NiQuitin®." See also, for example, U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; and U.S. Pat. No. 6,248,760 to Wilhelmsen; and US Pat. Pub. No. 2001/0016593 to Wilhelmsen, which are incorporated herein by reference.

It would be desirable to provide alternative compositions capable of delivering or administering nicotine via an oral route for therapeutic purposes.

SUMMARY OF THE INVENTION

In one aspect, the present invention relates to a nicotinic compound-containing composition intended to be employed for therapeutic purposes. The composition is typically in a pharmaceutically acceptable form adapted for oral delivery of the composition. The composition generally comprises a series of two or more different formulations having different properties that may be arranged in various ways. The different formulations comprising the product can be provided, for example, in a multi-layered form. For example, the nicotinic compound-containing composition can comprise an inner core of one formulation and one or more coatings of another formulation, which may be full or partial coatings. In this way, it is possible to combine formulations having different organoleptic properties within the same product to provide a unique composition. In certain embodiments, such multi-layered compositions afford a modified delivery profile during use. For example, certain formulations may provide for fast release of the nicotinic compound contained therein, whereas other formulations may provide for extended release of the nicotinic compound contained therein.

In one aspect of the invention is provided a multi-layered pharmaceutical composition comprising two or more formulations having different organoleptic properties, wherein the formulations are selected from the group consisting of: i) a dissolvable formulation comprising a sugar substitute in an amount of at least about 80% by weight and a sugar alcohol syrup; ii) a meltable formulation comprising a lipid having a melting point of about 36° C. to about 45° C.; iii) a pastille formulation comprising a polysaccharide filler; iv) a pastille formulation comprising a sugar alcohol and a natural gum binder component; v) a chewable formulation comprising a binder, an emulsifier, and a lipid having a melting point of about 36° C. to about 45° C.; and vi) a hard coating formulation comprising a binder, a sugar substitute, and a sugar alcohol syrup; wherein at least one formulation further comprises one or more nicotinic compounds. In certain embodiments, all formulations of the multi-layered pharmaceutical composition can comprise one or more nicotinic compounds, which may be the same or different.

In some embodiments, the one or more nicotinic compounds in the pharmaceutical compositions of the invention can be independently in the form of a free base, a salt, a complex, or a solvate. The one or more nicotinic compounds can comprise, for example, nicotine polacrilex. In certain embodiments, the one or more nicotinic compounds comprise a nicotinic compound sorbed onto a porous particulate carrier, which can comprise, for example, microcrystalline cellulose.

The form of the nicotinic compound-containing pharmaceutical composition can vary. For example, in some embodiments, the form of the pharmaceutical composition is a core formulation surrounded by one or more continuous layers or a core formulation coated by one or more discontinuous (e.g., partial) layers so as to form a layered or side-by-side configuration of the two or more formulations. The number of layers can vary; for example, the multi-layered pharmaceutical composition can in some embodiments comprise between two and ten layers, such as between two and five layers.

The components of the various formulations can vary. In some embodiments, the sugar substitute of the dissolvable formulation can comprise isomalt and/or the sugar alcohol syrup of the dissolvable formulation can comprise maltitol syrup. In one exemplary embodiment, the dissolvable formulation comprises a nicotinic compound; a sugar substitute in an amount of about 80% by weight or greater; and a sugar alcohol syrup.

The meltable formulation, where present, may in certain embodiments comprise a lipid having a melting point of about 38° C. to about 41° C. The lipid can be, for example, an animal or plant derived fat, wax, or oil. In one exemplary embodiment, the meltable formulation comprises a nicotinic compound, a lipid having a melting point of about 36° C. to about 45° C. in an amount of from about 10% to about 50% by weight; and a filler in an amount of from about 20% to about 40% by weight. In another exemplary embodiment, the meltable formulation comprises a nicotinic compound; a lipid having a melting point of about 36° C. to about 45° C. in an amount of about 30% by weight or greater; and a filler in an amount of about 30% by weight or greater.

The pastille formulation iii), where present, may in certain embodiments comprise polydextrose as the polysaccharide filler component. The polysaccharide filler component in some embodiments can be present in an amount of from about 10 weight percent to about 25 weight percent of the pastille formulation on a dry weight basis. In one exemplary embodiment, the pastille formation iii) comprises a nicotinic compound; a polysaccharide filler in an amount of about 10% by weight or greater, a humectant in an amount of about 20% by weight or greater; a binder in an amount of about 10% by weight or greater; and an emulsifier in an amount of about 1% by weight or greater.

In one exemplary embodiment, the pastille formation iv) comprises a nicotinic compound; humectant in an amount of about 0.5% by weight or greater; sugar alcohol filler in an amount of about 20% by weight or greater; and a natural gum binder in an amount of about 10% or greater.

The chewable formulation, where present, may in certain embodiments comprise gum arabic as the binder material. In one exemplary embodiment, the chewable formulation comprises a nicotinic compound, a binder material in an amount of about 30% by weight or greater, and a lipid having a melting point of about 36° C. to about 45° C. in an amount of about 15% by weight or greater.

The hard coating formulation, where present, may in certain embodiments comprise carboxymethylcellulose as the binder component. The hard coating formulation, where present, may in certain embodiments comprise isomalt as the sugar substitute. In one exemplary embodiment, the hard coating formulation comprises a nicotinic compound; a binder; a sugar substitute in an amount of about 20% by weight or greater; and a sugar alcohol syrup in an amount of about 5% by weight or greater.

Any combination of two or more formulations as described herein can be used within the multi-layered pharmaceutical compositions of the invention. For example, the product may, in certain embodiments, comprise two different formulations, wherein the formulations comprise: formulations i) and ii), formulations i) and iii), formulations i) and iv), formulations i) and v), formulations i) and vi), formulations ii) and iii), formulations ii) and iv), formulations ii) and v), formulations ii) and vi), formulations iii) and iv), formulations iii) and v), formulations iii) and vi), formulations iv) and v), or formulations iv) and vi), wherein the formulations can be arranged in any manner. For the foregoing, the listed formulations are meant to include permutations thereof and the formulations can be structured in various ways with respect to each other. For example, "formulation i) and ii)" can also include formulation ii) and formulation i), and "formulations iv) and vi)" can also include formulation vi) and formulation iv). In other words, "formulations i) and ii)" is intended to cover embodiments wherein formulation i) is the core and formulation ii) is a partial or complete layer thereon as well as embodiments wherein formulation ii) is the core and formulation i) is a partial or complete layer thereon.

In certain embodiments, combinations of three or more formulations as described herein can be used within the multi-layered pharmaceutical compositions of the invention. In certain embodiments, the product may comprise formulations i), ii), and iii); formulations i), ii), and iv); formulations i), ii), and v); formulations i), ii), and vi); formulations i), iii), and iv); formulations i), iii), and v); formulations i), iii), and vi); formulations i), iv), and v); formulations i), iv), and vi); formulations i), v), and vi); formulations ii), iii), and iv); formulations ii), iii), and v); formulations ii), iii), and vi); formulations ii), iv), and v); formulations ii), iv), and vi); formulations ii), v), and vi); formulations iii), iv), and v); formulations iii), iv), and vi); or formulations iii), v), and vi), wherein the formulations can be arranged in any manner. For the foregoing, the listed formulations are meant to include permutations thereof and the formulations can be structured in various ways with respect to each other. For example, "formulations i), ii), and iii)" can also include formulation i), iii), and ii); formulation ii), iii), and i); formulation ii), i), and iii); formulation iii), i), and ii), and formulation iii), ii), and i). In other words, "formulations i), ii), and iii)" is intended to cover embodiments wherein formulation i) is the core, formulation ii) is a partial or complete layer on formulation i), and formulation iii) is a partial or complete layer on formulation ii), as well as embodiments wherein formulation i) is the core, formulation iii) is a partial or complete layer on formulation i), and formulation ii) is a partial or complete layer on formulation iii), as well as embodiments wherein formulation ii) is the core, formulation iii) is a partial or complete layer on formulation ii), and formulation i) is a partial or complete layer on formulation iii), as well as embodiments wherein formulation ii) is the core, formulation i) is a partial or complete layer on formulation ii), and formulation iii) is a partial or complete layer on formulation ii), as well as embodiments wherein formulation iii) is the core, formulation i) is a partial or complete layer on formulation iii), and formulation ii) is a partial or complete layer on formulation i), as well as embodiments wherein formulation iii) is the core, formulation ii) is a partial or complete layer on formulation iii), and formulation i) is a partial or complete layer on formulation ii).

In another aspect of the invention is provided a process for preparing a multi-layered pharmaceutical composition, comprising: preparing a first formulation by combining a nicotinic compound with one or more components selected from the group consisting of binders, lipid components, polysaccharide fillers, sugar substitutes, sugar alcohol syrups, flavorants, sweeteners, emulsifiers, disintegration aids, humectants, buffering agents, and mixtures thereof to form a first nicotinic compound-containing mixture and forming the first nicotinic compound-containing mixture into a desired form; preparing a second formulation by combining a nicotinic compound with one or more components selected from the group consisting of binders, lipid components, polysaccharide fillers, sugar substitutes, sugar alcohol syrups, flavorants, sweeteners, emulsifiers, disintegration aids, humectants, buffering agents, and mixtures thereof to form a second nicotinic compound-containing mixture and forming the second nicotinic compound-containing mixture into a desired form; and applying the second formulation to the first formulation, wherein the formulations are selected from formulations i), ii), iii), iv), v), and iv), as described herein.

In certain embodiments, the first formulation can be formed into a desired form by pouring or otherwise introducing the first nicotinic compound-containing mixture into a mold, injection molding the first nicotinic compound-containing mixture, or other suitable means for providing a formulation. In certain embodiments, the second formulation can be applied by spray coating, dip coating, or by forming the second formulation into a sheet that is applied to the first formulation as a sandwiched coating. Spray coating or dip coating can be conducted at a temperature such that the first formulation is maintained in substantially intact form. In some embodiments, the method further comprises applying a third formulation as a coating on the second formulation. The third nicotinic compound-containing formulation can be applied, for example, by spray coating, dip coating, or by forming the third nicotinic compound-containing formulation into a sheet that is applied to the second formulation as a sandwiched coating.

DETAILED DESCRIPTION OF THE PREFERRED EMBODIMENTS

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

According to the invention, a nicotinic compound pharmaceutical composition is provided which comprises at least two different formulations. Specifically, such compositions generally comprise formulations with different organoleptic properties, such as multi-layered pharmaceutical compositions, wherein two or more formulations are provided as layers of the pharmaceutical compositions. Each formulation within the nicotinic compound-containing composition can comprise one or more nicotinic compounds. Although at least one formulation within the nicotinic compound-containing composition comprises a nicotinic compound, in certain embodiments, one or more other formulations (e.g., one or more layers) within the composition can be essentially (including completely) free of nicotinic compounds. The invention further provides processes for preparing multi-layered nicotinic compound-containing pharmaceutical compositions.

By "layered" is meant that the structure of the multi-layered pharmaceutical composition is generally that of a core, surrounded by one or more coating layers, which may be partial or complete layers. In other words, each coating layer may completely coat the core or previous layer or may only cover portions thereof. The core can be any shape, such as a flattened sheet or structure of a given shape (e.g., square, round, oval, oblong, or rectangular) or a shape that can be described generally as spherical, cylindrical (e.g., ranging form the general shape of a flattened disc to the general shape of a relatively long, slender stick), helical, obloid, or the like). In some embodiments, the core and/or multi-layered pharmaceutical composition can have the form of a bead, granular powder, capsule, film, strip, gel, or the like. The shape of the composition can, in certain embodiments, resemble a wide variety of pill, tablet, lozenge, capsule, and caplet types of products. It is noted that side-by-side type configurations are also intended to be encompassed within the present invention, e.g., wherein the composition comprises two layers adhered together along one surface and, optionally, additional layers adhered to one or both of those two layers. The number of layers comprising the pharmaceutical composition can vary but typically is about 2 to about 10, such as 2, 3, 4, 5, 6, 7, 8, 9, or 10 layers. It is noted that although the pharmaceutical composition is described herein as "layered" or "multi-layered," the layers may not be discrete layers of different formulations, with clear demarcation between the layers. For example, there may be some degree of mingling between the formulations comprising adjacent layers of the product. However, in preferred embodiments, the pharmaceutical composition retains properties and behaviors of the individual formulations.

The organoleptic properties of the one or more formulations that make up the multi-layered pharmaceutical compositions generally vary. By "organoleptic" as used herein is meant any aspects that may be associated with the pharmaceutical composition formulations as experienced by the senses of the user. Organoleptic properties include, but are not limited to, taste, smell, mouthfeel (e.g., texture, dissolvability/meltability, firmness, resilience, crunchiness, chewiness) and the like. For example, the formulations within a given multi-layered pharmaceutical composition can, in certain embodiments, have organoleptic properties independently selected from hard, dissolvable, chewable, chewy, meltable, crisp, and combinations thereof. Certain formulations useful as components of a pharmaceutical composition according to the invention can be described as lozenge-like or pastille-like. The resulting multi-layered pharmaceutical composition can, in certain embodiments, comprise a unique mixture of organoleptic properties as a result of the combination of formulations having varying organoleptic properties. For example, in one specific embodiment, the pharmaceutical composition may have a hard, lozenge-like outer formulation and a meltable core formulation such that, when placed into the mouth of the user, the user initially experiences a dissolving effect and later in use, experiences a melting effect. It is noted that numerous other combinations of formulations providing varying combinations of organoleptic properties are encompassed herein.

As used herein, the terms "dissolve," "dissolving," and "dissolvable" refer to formulations having aqueous-soluble components that interact with moisture in the oral cavity and enter into solution, thereby causing gradual consumption of the product.

As used herein, "melt," "melting," and "meltable" refer to the ability of the formulation to change from a solid state to a liquid state. That is, melting occurs when a substance (e.g., the formulation within a pharmaceutical composition) changes from solid to liquid, usually by the application of heat. The application of heat in regard to the pharmaceutical composition of the present invention is provided by the internal temperature of a user's mouth. Thus, the term "meltable" refers to a formulation that is capable of liquefying in the mouth of the user as the product changes phase from solid to liquid, and is intended to distinguish formulations and/or products that merely disintegrate in the oral cavity through loss of cohesiveness within the formulation or formulations that merely dissolve in the oral cavity as aqueous-soluble components of the formulation interact with moisture.

As used herein, the term "pastille" refers to a dissolvable oral formulation made by solidifying a liquid or gel composition, such as a composition that includes a gelling or binding agent, so that the final product is a hardened solid gel. In certain embodiments, such formulations are characterized by sufficient cohesiveness to withstand light chewing action in the oral cavity without rapidly disintegrating. Pastille-like formulations of the disclosure typically do not exhibit a highly deformable chewing quality as found in conventional chewing gum.

As used herein, "chewable" means deformable in the mouth with a cohesiveness greater than that of a pastille, but generally less than that of a gum. Such formulations may be characterized by sufficient cohesiveness to withstand a greater extent of chewing than a pastille; however, such compositions generally disintegrate in the oral cavity (unlike gum formulations).

As used herein, "hard coating-like" means a layer that exhibits some degree of hardness and/or crunchiness. It is generally a somewhat thin layer, allowing it to be easily broken by teeth of the user and/or readily dissolved in the mouth of the user. Although it is referred to herein as a "coating," it is noted that this layer need not comprise an exterior layer of the pharmaceutical composition, and may comprise an interior layer of the product.

The one or more "nicotinic compounds" within the pharmaceutical formulations of the present invention are naturally occurring or synthetic nicotine unbound from a plant material, meaning the compound is at least partially purified and not contained within a plant structure such as a tobacco leaf. Most preferably, nicotine is naturally-occurring and obtained as an extract from a *Nicotiana* species (e.g., tobacco). Exemplary types of tobacco and manners of processing the tobacco are set forth in U.S. patent application Ser. No. 13/240,500 to Holton, Jr. et al., filed Sep. 22, 2011, and which is incorporated herein by reference. See also the nicotine-containing compositions set forth in US Pat. Pub. Nos. 2011/0268809 to Brinkley et al. and 2011/0274628 to Borschke, as well as U.S. patent application Ser. No. 13/278,877 to Borschke et al, filed Oct. 21, 2011, all of which are incorporated by reference herein.

The nicotine can have the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine) or a racemic mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis. Despite the fact that nicotine can be extracted from *Nicotiana* species, it is highly preferred that the nicotine (and the composition and products produced in accordance with the present invention) is virtually or essentially absent of other components of tobacco.

In embodiments wherein nicotine is derived from a plant of the *Nicotiana* species, the plant or portions thereof can be subjected to various types of processing conditions to provide the nicotine. For example, components can be separated from one another, or otherwise fractionated into chemical classes or mixtures of individual compounds. Typical separation processes can include one or more process steps (e.g., solvent extraction using polar solvents, organic solvents, or supercritical fluids), chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated herein by reference. See also, the types of separation techniques set forth in Brandt et al., *LC-GC Europe*, p. 2-5 (March, 2002) and Wellings, *A Practical Handbook of Preparative HPLC* (2006), which are incorporated by reference. In addition, the plant or portions thereof can be subjected to the types of treatments set forth in Ishikawa et al., *Chem. Pharm. Bull.,* 50, 501-507 (2002); Tienpont et al., *Anal. Bioanal. Chem.,* 373, 46-55 (2002); Ochiai, *Gerstel Solutions Worldwide*, 6, 17-19 (2006); Coleman, III, et al., *J. Sci. Food and Agric.,* 84, 1223-1228 (2004); Coleman, III et al., *J. Sci. Food and Agric.,* 85, 2645-2654 (2005); Pawliszyn, ed., *Applications of Solid Phase Micro extraction, RSC Chromatography Monographs*, (Royal Society of Chemistry, UK) (1999); Sahraoui et al., *J. Chrom.,* 1210, 229-233 (2008); and 5,301,694 to Raymond et al., which are all incorporated herein by reference.

In certain embodiments, isolation of nicotine from a plant of the *Nicotiana* species comprises a step of removing high molecular weight components from a tobacco extract. In certain embodiments, high molecular weight components that are beneficially removed according to the present invention include, but are not limited to, high molecular weight Maillard browning polymers, proteins, polysaccharides, certain pigments, and bacteria. Various methods can be used for this purpose, including size exclusion chromatography, microfiltration, ultrafiltration, nanofiltration, reverse osmosis, and combinations thereof.

In one embodiment, ultrafiltration is used to remove high molecular weight components from tobacco material. The ultrafiltration method is typically applied to a tobacco material in the form of a tobacco extract (e.g., an aqueous tobacco extract). In ultrafiltration, the material to be filtered is brought into contact with a semipermeable membrane as described in more detail in Ser. No. 13/240,500 to Holton, Jr. et al., filed Sep. 22, 2011, which is incorporated herein by reference. In such embodiments, the ultrafiltration step is designed to achieve a tobacco extract having a decreased level of suspended solids, and thus an increased level of clarity.

Commercial ultrafiltration systems are readily available and may be used in some embodiments for ultrafiltration of tobacco extracts. For example, commercial suppliers such as Millipore, Spectrum® Labs, Pall Corporation, Whatman®, Porex Corporation, and Snyder Filtration manufacture various filter membranes and cartridges, and/or filtration systems (e.g., tangential flow filtration systems). Exemplary membranes include, but are not limited to, Biomax® and Ultracel® membranes and Pellicon® XL cassettes (from Millipore), Microkros®, Minikros®, and KrosFlo® Hollow Fiber Modules (from Spectrum® Labs), and Microza filters and Centramate,™ Centrasette,™ Maximate™, and Maxisette™ Tangential Flow Filtration Membrane Cassettes. Commercially available filtration systems include, but are not limited to, Millipore's Labscale™ Tangential Flow Filtration (TFF) system and Spectrum® Labs' KrosFlo® and MiniKros® Tangential Flow Filtration Systems.

Filters and/or membranes that may be useful according to the present invention include those with molecular weight cutoffs of less than about 100,000 Da, less than about 75,000 Da, less than about 50,000, less than about 25,000 Da, less than about 20,000 Da, less than about 15,000 Da, less than about 10,000 Da, and less than about 5,000 Da. In certain embodiments, a multistage filtration process is used to provide an extract with improved clarity. Such embodiments employ multiple filters and/or membranes of different (typically decreasing) molecular weight cutoffs. Any number of filters and/or membranes can be used in succession according to the invention. For example, a first filtration may be conducted using a 50,000 Da molecular weight cutoff filter and a second filtration may be conducted using a 5,000 Da molecular weight cutoff filter. Thus, depending on the molecular weight cutoff of the filters, the ultrafiltered extract may comprise only compounds with molecular weights below about 50,000, below about 25,000, below about 10,000 Da, below about 7,500 Da, below about 5,000 Da, below about 2,500 Da, or below about 1,000 Da. The ultrafiltered extract typically comprises primarily sugars, nicotine, and amino acids. Ultrafiltration can be used in combination with other separation and purification methods to provide nicotine having an acceptable purity level.

The ultrafiltered extract may exhibit a level of improvement in clarity over the non-ultrafiltered extract. Clarity of the extract, and compositions according to the invention made therefrom, is typically defined in terms of translucency. As used herein, "translucent" or "translucency" refers to materials allowing some level of light to travel therethrough diffusely. In various embodiments, certain materials of the invention (e.g., certain tobacco extracts or nicotine obtained therefrom can have such a high degree of clarity that the material or a portion thereof can be classified as "transparent" or exhibiting "transparency," which is defined as a material allowing light to pass freely through without significant diffusion. The clarity of the ultrafiltered extract is such that there is some level of translucency as opposed to opacity (which refers to materials that are impenetrable by light). In certain embodiments, the ultrafiltered extract is visually analyzed or is analyzed by contacting the extract with light and measuring the percent of light that has not been absorbed and/or dispersed by the extract. The measurement can be done, for example, using a standard spectrophotometer at a given wavelength. The spectrophotometer is typically calibrated with deionized water, which is assigned a transparency value of 100%. Ultrafiltered extract may, in some embodiments, exhibit a translucency of greater than about 5%, greater than about 10%, greater than about 15%, greater than about 20%, greater than about 25%, greater than about 30%, greater than about 40%, greater than about 50%, greater than about 60%, greater than about 60%, greater than about 70%, greater than about 80%, or greater than about 90%. Typically, the ultrafiltered extract will not be colorless, and will have some discernible brown/black coloring. Following ultrafiltration, the extract can be stored in the refrigerator or freezer or the extract can be freeze dried or spray dried prior to use in the compositions of the invention. In certain embodiments, it is provided in syrup form. The ultrafiltered extract in some embodiments can be further treated to provide a nicotinic compound in a sufficient level of purity.

Nicotinic compounds of the invention can include nicotine in free base form, salt form, as a complex, or as a solvate. See, for example, the discussion of nicotine in free base form in US Pat. Pub. No. 2004/0191322 to Hansson, which is incorporated herein by reference. At least a portion of the nicotinic compound can be employed in the form of a resin complex of nicotine where nicotine is bound in an ion exchange resin such as nicotine polacrilex. See, for example, U.S. Pat. No. 3,901,248 to Lichtneckert et al.; which is incorporated herein by reference. At least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.,* 12, 43-54 (1983). Additionally, salts of nicotine have been available from sources such as Pfaltz and Bauer, Inc. and K&K Laboratories, Division of ICN Biochemicals, Inc. Exemplary pharmaceutically acceptable nicotine salts include nicotine salts of tartrate (e.g., nicotine tartrate and nicotine bitartrate) chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. In certain embodiments, at least a portion of the nicotinic compound is in the form of a salt with an organic acid moiety, including, but not limited to, levulinic acid as discussed in US Pat. Pub. No. 2011/0268809 to Brinkley et al., which is incorporated herein by reference.

In one embodiment, the nicotinic compound is sorbed onto a porous particulate carrier material, such as microcrystalline cellulose (MCC) prior to incorporation within the compositions of the invention. In one embodiment, the MCC materials used in the invention have an average particle size range of about 15 to about 250 microns. Exemplary MCC materials include various grades of AVICEL® and VIVACEL® materials. See, for example, US Pat. Pub. No. 2004/

0191322 to Hansson, which is incorporated by reference herein. In certain embodiments, multiple forms of nicotinic compounds could be sorbed onto the particulate carrier, including any of the various nicotinic compound combinations discussed herein. In some embodiments, the nicotinic compound and, optionally, an organic acid moiety can be sorbed onto the particulate carrier by, for example, dissolving the nicotinic compound (and, optionally, an organic acid moiety) in a hydrophilic solvent (such as water, alcohol, or mixtures thereof) and combining the solution with the particulate carrier, followed by drying to remove the solvent. The particulate carrier material with the sorbed nicotine and, optionally, organic acid moiety, can be combined with other carriers or excipients in order to provide a composition adapted for oral delivery of the active ingredient.

The compositions of the invention possess a form that is pharmaceutically effective and pharmaceutically acceptable. That is, the composition most preferably does not incorporate to any appreciable degree, or does not purposefully incorporate, components of tobacco, other than nicotine. As such, pharmaceutically effective and pharmaceutically acceptable compositions do not include tobacco, processed tobacco components, or many of the components of tobacco traditionally present within tobacco-containing cigarettes, cigars, pipes, or smokeless forms of tobacco products. Highly preferred compositions include less than 0.5 weight percent of tobacco components other than nicotine, more often less than about 0.25 weight percent, and typically are entirely absent or devoid of components of tobacco, processed tobacco components, or components derived from tobacco, other than nicotine.

According to the invention, nicotinic compounds in one or more of the various forms as described herein are used in the production of pharmaceutical compositions. Specifically, a nicotinic compound can be combined with one or more additional components to give a formulation that is used in combination with other nicotinic compound-containing or non-nicotinic compound-containing formulations to provide the multi-layered pharmaceutical compositions of the present invention. The types of formulations included within a pharmaceutical composition according to the invention can vary, and can include, but are not limited to, lozenge-type formulations, meltable-type formulations, chewable-type formulations, hard coating-type formulations, and starch-molded and injection molded formulations. Each formulation can contain one or more nicotinic compounds or can be free of nicotinic compounds. However, at least one component of the multi-layered pharmaceutical composition typically comprises a nicotinic compound.

The components of each formulation in the multi-layered pharmaceutical composition can vary and are independently selected such that the two or more formulations generally comprise different combinations of other components. The individual components (including, optionally, one or more nicotinic compounds) can be processed, blended, formulated, combined and/or mixed to produce the desired formulation.

The other components of the formulations can be artificial or can be obtained or derived from herbal or biological sources. Exemplary types of components that can be incorporated within one or more formulations according to the invention include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, lactose, and the like), artificial sweeteners (e.g., sucralose, saccharin, aspartame, acesulfame K, neotame and the like), organic and inorganic fillers (e.g., grains, processed grains, puffed grains, maltodextrin, dextrose, calcium carbonate, calcium phosphate, calcium polycarbofil, corn starch, lactose, sugar alcohols such as isomalt, mannitol, xylitol, or sorbitol, finely divided cellulose, hydroxypropylcellulose, vegetable protein, silicon dioxide, and the like), film formers and binders (e.g., povidone, sodium carboxymethylcellulose, hydroxypropylcellulose, hydroxypropylmethylcellulose, and other modified cellulosic types of binders, sodium alginate, acacia, xanthan gum, starch-based binders (e.g., potato starch, maize starch, etc.), gum arabic, gellan gum, lecithin, and the like), gelling agents (e.g., fish gelatin), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), emulsifiers, colorants (e.g., dyes and pigments, including caramel coloring, titanium dioxide, D&C Yellow No. 10, and the like), humectants (e.g., glycerin, propylene glycol, and the like), oral care additives (e.g., thyme oil, eucalyptus oil, and zinc), preservatives and antioxidants (e.g., potassium sorbate, sodium benzoate, ascorbyl palmitate, and the like), syrups (e.g., honey, high fructose corn syrup, and the like), thickeners, disintegration or compressibility aids (e.g., microcrystalline cellulose, croscarmellose sodium, crospovidone, sodium starch glycolate, pregelatinized corn starch, and the like), lubricants or processing aids (e.g., magnesium stearate or calcium stearate), antiadherents (e.g., talc), glidants (e.g., colloidal silica), surfactants (e.g., polysorbate 80), flavorant and flavoring mixtures, and mixtures thereof. Exemplary types of components may include those described in, for example, U.S. Pat. Pub. No. 2010/0291245 to Gao et al., which is incorporated herein by reference.

The pharmaceutical compositions of the invention may be conveniently made available in a unit dosage form, whereby such formulations may be prepared by any of the methods generally known in the pharmaceutical arts. Generally speaking, such methods of preparation comprise combining (by various methods) an active agent with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

The nicotine-containing pharmaceutical compositions of the invention can incorporate various pharmaceutically acceptable excipients. By "pharmaceutically acceptable carrier" or "pharmaceutically acceptable excipient" is intended a carrier or excipient that is conventionally used in the art to facilitate the storage, administration, and/or the healing effect of an active agent (e.g., a nicotinic compound). The carrier(s) must be pharmaceutically acceptable in the sense of being compatible with the other ingredients of the formulation and not unduly deleterious to the recipient thereof. A carrier may also reduce any undesirable side effects of the agent. See, Wang et al. (1980) *J. Parent. Drug Assn.* 34(6):452-462, herein incorporated by reference in its entirety. Other exemplary pharmaceutical excipients and/or additives suitable for use in the compositions according to the invention are listed in Remington: The Science & Practice of Pharmacy, 21$^{st}$ ed., Lippincott Williams & Wilkins (2006); in the Physician's Desk Reference, 64$^{th}$ ed., Thomson PDR (2010); and in Handbook of Pharmaceutical Excipients, 6$^{th}$ ed., Eds. Raymond C. Rowe et al., Pharmaceutical Press (2009), which are incorporated herein by reference.

The various excipients can vary, and the selection and amount of each excipient can depend upon factors such as the ultimate form and function of product that is desired. See, for example, the types of ingredients, relative amounts and combinations of ingredients, nicotine-containing formulations and preparation processes for nicotine-containing products set forth in U.S. Pat. No. 5,512,306 to Carlsson et al.; U.S. Pat. No. 5,525,351 to Dam; U.S. Pat. No. 5,549,906 to Santus; U.S. Pat. No. 5,711,961 to Reiner et al.; U.S. Pat. No. 5,811,126 to Krishnamurthy; U.S. Pat. No. 5,939,100 to Albrechtsen et al.; U.S. Pat. No. 6,024,981 to Khankari et al.; U.S. Pat. No. 6,083,531 to Humbert-Droz et al.; U.S. Pat. No. 6,090,401 to Gowan, Jr. et al.; U.S. Pat. No. 6,110,495 to Dam; U.S. Pat. No. 6,248,760 to Wilhelmsen; U.S. Pat. No. 6,280,761 to Santus; U.S. Pat. No. 6,426,090 to Ream et al.; U.S. Pat. No. 6,569,463 to Patel et al.; U.S. Pat. No. 6,583,160 to Smith et al.; U.S. Pat. No. 6,585,997 to Moro et al.; U.S. Pat. No. 6,676,959 to Andersson et al.; U.S. Pat. No. 6,893,654 to Pinney et al.; U.S. Pat. No. 7,025,983 to Leung et al.; and U.S. Pat. No. 7,163,705 Johnson et al.; US Pat. Pub. Nos. 2003/0176467 to Andersson et al.; 2003/0235617 to Martino et al.; 2004/0096501 to Vaya et al.; 2004/0101543 to Liu et al.; 2004/0191322 to Hansson; 2005/0053665 to Ek et al.; 2005/0123502 to Chan et al.; 2008/0038209 to Andersen et al.; 2008/0286341 to Andersson et al.; 2009/0023819 to Axelsson; 2009/0092573 to Andersen; 2010/0004294 to Axelsson et al.; and 2010/0061940 to Axelsson et al.; which are incorporated herein by reference.

The foregoing components can be provided in a powder or granulated form for mixing with the one or more nicotinic compounds, or otherwise may be provided in liquid form. Most preferably, the components when provided in a powder or granulated form are employed in the form of parts or pieces that have an average particle size less than about 50 microns. According to some aspects, the average particle size of the components may be about 25 microns or less. The moisture content of the components provided in a powder or granulated form may vary. Most preferably, the moisture content of the components provided in a powder or granulated form is less than about 10 weight percent, and may be less than about 5 percent, and is often less than about 2.5 weight percent. The components may be admixed with the nicotine in, for example, a Hobart mixer with a paddle prior to adding any liquid components. In the event liquid components are provided, the resultant mixture may still have a relatively low moisture content of less than about 10 weight percent, and may be less than about 5 percent, and is often less than about 2.5 weight percent. The relative amounts of the various additive components within the pharmaceutical composition may vary.

The aforementioned types of components can be employed together (e.g., as component formulations) or separately (e.g., individual components can be added at different stages involved in the preparation of the nicotinic compound-containing formulation and the final pharmaceutical product). The relative amounts of the various components within the nicotinic compound-containing formulation may vary, and typically are selected so as to provide the desired sensory and performance characteristics to the pharmaceutical composition. Furthermore, the aforementioned types of components may be encapsulated as provided in the final product or composition. Exemplary encapsulated components are described, for example, in WO 2010/132444 A2 to Atchley, which has been incorporated by reference herein.

As used herein, a "flavorant" or "flavoring agent" is any flavorful or aromatic substance capable of altering the sensory characteristics associated with the pharmaceutical composition. Exemplary sensory characteristics that can be modified by the flavorant include, taste, mouthfeel, moistness, coolness/heat, and/or fragrance/aroma. The flavorants can be natural or synthetic, and the character of these flavors can be described as, without limitation, fresh, sweet, herbal, confectionary, floral, fruity or spice. Specific types of flavors include, but are not limited to, vanilla, coffee, chocolate, cream, mint, spearmint, menthol, peppermint, wintergreen, lavender, cardamon, nutmeg, cinnamon, clove, cascarilla, sandalwood, honey, jasmine, ginger, anise, sage, licorice, lemon, orange, apple, peach, lime, cherry, and strawberry. Flavorants utilized in the invention also can include components that are considered moistening, cooling or smoothening agents, such as eucalyptus. These flavors may be provided neat (i.e., alone) or in a composite (e.g., spearmint and menthol or orange and cinnamon). In some instances, the flavorant may be provided in a spray-dried form. Flavorants are typically present in an amount of about 0.5 to about 10 dry weight percent, often about 1 to about 6 dry weight percent, and most often about 2 to about 5 dry weight percent.

Sweeteners can be used in natural or artificial form or as a combination of artificial and natural sweeteners. In one embodiment, sucralose, sucrose, or a combination thereof is the primary sweetener ingredient. When present, a representative amount of sweetener, whether an artificial sweetener and/or natural sugar, may make up at least about 0.2 percent, at least about 1 percent, or at least about 5 percent, of the total dry weight of the composition. Preferably, the amount of sweetener within the composition will not exceed about 40 percent, often will not exceed about 35 percent, and frequently will not exceed about 30 percent, of the total dry weight of the composition.

Sucrose can be a particularly advantageous sweetener in certain embodiments (e.g., as a component of a starch-molded type formulation) as it is believed to contribute to the chewing resistance or "bounce" of the final product. In addition, while granulated sucrose provides far less sweetening effect as compared to sucralose, the presence of sucrose can be advantageous as an additional filler component. When these two sweeteners are present together, the sucralose is typically present in an amount of at least about 0.25 dry weight percent, often at least about 0.5 dry weight percent, and most often at least about 1.0 dry weight percent (e.g., about 0.25 to about 2.0 dry weight percent), and the sucrose is typically present in an amount of at least about 2.0 dry weight percent, often at least about 3.0 dry weight percent, and most often at least about 4.0 dry weight percent (e.g., about 1.0 to about 6.0 dry weight percent).

In certain embodiments, some formulations (or the entire pharmaceutical composition) are sugar-free, comprising one or more sugar substitutes. "Sugar-free" as used herein is intended to include products having less than about 1/15th sugar by weight, or less than about 1/10th sugar by weight. A sugar substitute, where used, may be provided in pure, solid form (e.g., granular or powdered form). In certain embodiments, the sugar substitute is dry, comprising a very low water content. For example, the sugar substitute can comprise less than about 5% water by weight, less than about 3% water by weight, less than about 2% water by weight, or less than about 1% water by weight.

In some embodiments, a syrup (e.g., corn syrup) preferably may be employed in an amount sufficient to provide desired flavor attributes to the pharmaceutical composition. In some embodiments (e.g., in starch molded type formulations), syrup may be employed in amounts sufficient to provide chewiness and retard solubilization. A representative amount of syrup (e.g., high fructose corn syrup) may make up less than about 10 percent or less than about 5 percent of the total dry weight of the composition.

In certain embodiments, a sugar syrup or sugar alcohol syrup is added to a lozenge-type formulation to affect the re-crystallization of another component of the formulation during preparation (e.g., a melted sugar substitute). Exemplary sugar alcohol syrups for such purposes include maltitol syrup, xylitol, mannitol, glycerol, erythritol, threitol, arabitol, ribitol, mannitol, sorbitol, dulcitol, iditol, isomalt, lactitol, and polyglycitol syrups. Other syrups, such as corn syrup, golden syrup, or molasses can be used. The amount of sugar alcohol syrup can vary, but typically ranges from about 0.1% to about 2%, often from about 0.5% to about 1.5%, and more often about 1% by weight of the pharmaceutical composition mixture. In certain embodiments, the amount of sugar alcohol syrup is higher, for example, up to about 2% by weight of the mixture, up to about 5% by weight of the mixture, up to about 10% by weight of the mixture, or up to about 20% by weight of the mixture The pharmaceutical composition of the present disclosure may typically include at least one filler ingredient. When a polysaccharide filler component is present, the optional filler ingredient may be provided in addition to the polysaccharide filler component. Such filler components of the composition often fulfill multiple functions, such as enhancing certain organoleptic properties such as texture and mouthfeel, enhancing cohesiveness or compressibility of the product, and the like. In certain embodiments (e.g., in starch molded-type formulations), sugar alcohols are particularly advantageous as filler components as they contribute some sweetness and do not disrupt the desired chewable characteristics of the final product. Sugar alcohols (e.g., isomalt) are polyols derived from monosaccharides or disaccharides that have a partially or fully hydrogenated form. Exemplary sugar alcohols have between about 4 and about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). A sugar alcohol can be added in the form of an aqueous solution or suspension, such as a solution or suspension with a solids content of about 50 to about 90 weight percent. Combinations of a sugar alcohol with a further filler component can also be used. When present, a representative amount of filler, whether an organic and/or inorganic filler, may make up at least about 10 percent, at least about 20 percent, or at least about 25 percent, based on the total dry weight of the composition. Preferably, the amount of additional filler within the composition will not exceed about 50 percent, and frequently will not exceed about 40 percent, of the total dry weight of the composition. In one embodiment, a sugar alcohol such as sorbitol is provided as an additional filler.

A salt (e.g., sodium chloride, flour salt) may be employed in amounts sufficient to provide desired sensory attributes to the pharmaceutical composition. When present, a representative amount of salt is at least about 0.5 dry weight percent or at least about 1.0 dry weight percent or at least about 1.5 dry weight percent, but will typically make up less than about 5 percent of the total dry weight of the composition (e.g., about 0.5 to about 4 dry weight percent). In some embodiments, the salt, when present, will make up less than about 2 percent or less than about 1 percent of the total dry weight of the composition.

A humectant (e.g., glycerin) may be employed in amounts sufficient to provide desired moisture attributes to the pharmaceutical composition. Further, in some instances, the humectant may impart desirable flow characteristics to the pharmaceutical composition (e.g., for depositing in a starch mould). When present, a representative amount of humectant will typically make up at least about 1 percent of the total dry weight of the composition, at least about 1.5 dry weight percent, or at least about 2 dry weight percent. In certain embodiments, the amount of humectant is at least about 10 dry weight percent or at least about 20 dry weight percent. An exemplary dry weight range is about 1 to about 40 weight percent, more often about 3 to about 35 dry weight percent. In some embodiments, the humectant is provided in am amount of less than about 5 percent of the total dry weight of the composition (e.g., about 0.5 to about 4 dry weight percent). A binder (or combination of binders) may be employed in amounts sufficient to provide the desired physical attributes and physical integrity to the pharmaceutical composition. When present, a representative amount of binder may make up at least about 5 percent, at least about 10 percent, at least about 15 percent, at least about 20 percent, or at least about 25 percent of the total dry weight of the composition. Preferably, the amount of binder within the composition will not exceed about 35 percent, about 40 percent, or about 45 percent of the total dry weight of the composition. Often, the amount of binder within a desirable composition will not exceed about 20 percent, and frequently will not exceed about 15 percent, of the total dry weight of the composition. In certain embodiments, the binder material includes a natural gum. As used herein, a natural gum refers to polysaccharide materials of natural origin that are useful as thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof.

An emulsifier may be employed in amounts sufficient to provide desired stabilization attributes to the pharmaceutical composition. When present, a representative amount of emulsifier will typically make up less than about 5 percent of the total dry weight of the composition.

Certain buffering agents buffer within a pH range of about 6 to about 10, and exemplary buffering agents include metal hydroxides, metal carbonates, metal bicarbonates, or mixtures thereof. The buffering agent, where present, is typically present in an amount less than about 1 percent based on the dry weight of the formulation. Various food-grade buffering agents are known and can be used to adjust the pH of the products of the present invention. Suitable buffering agents include those selected from the group consisting of acetates, glycinates, phosphates, glycerophosphates, citrates such as citrates of alkaline metals, carbonates, hydrogen carbonates, and borates, and mixtures thereof. In certain embodiments, the buffering agent is an amino acid, as taught for example, in US Pat. Pub. No. 2008/0286341 to Andersson et al. and PCT Appl. No. WO2008/040371 to Andersson et al., which are both incorporated herein by reference. As noted therein, various amino acids and salts thereof are useful for this purpose, including, but not limited to, arginine, asparigine, glutamic acid, glutamine, glycine, histidine, isoleucine, leucine, lysine, methionine, phenylalanine, serine, threonine, valine, cysteic acid, N-glycylglycine, and ornithine. In certain embodiments, N-glycylglycine or L-lysine is added as a buffering agent. In some embodiments, an amino acid buffering agent is used in combination with another amino acid buffering agent and/or in combination with one or more non-amino acid buffering agents. In certain embodiments, the optional pH adjusting agent is a base (e.g., NaOH). In certain embodiments, L-lysine and NaOH are added to the compositions of the present invention.

It is well-known that nicotine is subject to oxidation and accordingly, it may be advantageous to incorporate one or more anti-oxidants, such as, e.g., ascorbyl palmitate and/or sodium ascorbate, in a composition according to the invention. The one or more anti-oxidants may be present in a concentration of from about 0.05% to about 0.3% by weight, such as, e.g., from about 0.1% to about 0.25% or from about 0.15% to about 0.2% in the pharmaceutical composition mixture.

Formulations of the present invention may include short-term, rapid-onset, rapid-offset, controlled release, sustained release, delayed release, and pulsatile release formulations, providing the formulations achieve administration of a nicotinic compound as described herein. See *Remington's Pharmaceutical Sciences* (18$^{th}$ ed.; Mack Publishing Company, Eaton, Pa., 1990), which is incorporated herein by reference in its entirety.

Compositions of the present invention incorporate a pharmaceutically effective amount of nicotine. The dose of active ingredient (i.e., all the various nicotine forms) is preferably that amount effective to treat some symptoms of, or prevent occurrence of the symptoms of, the condition, disease, or disorder from which the subject or patient suffers. By "effective amount", "therapeutic amount" or "effective dose" is meant that amount sufficient to elicit the desired pharmacological or therapeutic effects, thus resulting in effective prevention or treatment of the condition, disease, or disorder. Thus, an effective amount of active ingredient is an amount sufficient to enter relevant regions of the body (e.g., to pass across the blood-brain barrier of the subject), to bind to relevant receptor sites in the CNS and PNS of the subject, and/or to elicit neuropharmacological effects (e.g., elicit neurotransmitter secretion, thus resulting in effective prevention or treatment of the condition, disease, or disorder). Prevention of the disorder is manifested, for example, by delaying the onset of the symptoms of the condition, disease, or disorder. Treatment of the disorder is manifested by, for example, a decrease in the symptoms associated with the condition, disease, or disorder or an amelioration of the reoccurrence of the symptoms thereof.

The amount of active ingredient within the overall composition can vary. For a composition intended for oral consumption by insertion into the mouth of the subject (e.g., a lozenge or the like), the amount of nicotine within each dosage piece or unit typically is at least about 0.5 mg, generally is at least 1 mg, often is at least about 1.5 mg, and frequently is at least about 2 mg; while the amount of nicotine within each piece typically does not exceed about 10 mg, generally does not exceed about 8 mg, often does not exceed about 6 mg, and frequently does not exceed about 5 mg, calculated as nicotine base. Exemplary types of such products can incorporate about 2 mg, about 2.5 mg, about 3 mg, about 3.5 mg, about 4 mg, and about 4.5 mg of nicotine per piece or unit, calculated as nicotine base. The amount of nicotine incorporated into any given formulation layer within a multi-layer composition can vary, and typically will be selected so as to provide an overall nicotine content within each product unit in the ranges noted above.

The specific components and amounts thereof in a given formulation will depend on the desired characteristics of that formulation. For example, the components can vary depending upon the desired flavor, texture, and other characteristics. Certain exemplary formulations are provided in more detail below. It is to be noted that these are only exemplary formulations and are not intended to be limiting of the invention.

For example, a typical lozenge-type formulation may comprise a nicotinic compound, a sugar substitute, and a sugar alcohol syrup. The sugar substitute (e.g., isomalt) is a non-hygroscopic sugar alcohol capable of forming a glassy matrix. In one particular embodiment of the present invention, a lozenge-type formulation comprises: a nicotinic compound; a sugar substitute in an amount of at least about 80% by weight; and a sugar alcohol syrup. In certain embodiments, the sugar substitute is present in an amount of at least about 85% by weight or at least about 90% by weight. In a specific embodiment, a lozenge-type formulation may comprise isomalt, maltitol syrup, a nicotinic compound, NaCl, and sucralose. In certain embodiments, the formulation is translucent. For more details on representative lozenge-type formulations, see U.S. patent application Ser. No. 13/240,525 to Holton, Jr. et al., filed on Sep. 22, 2011, which is incorporated herein by reference.

A typical meltable-type formulation generally comprises a nicotinic compound and a lipid. The lipid can vary and may be, for example, a fat, oil, or wax substance (or combination thereof), forming a portion of the formulation. The lipid components can be derived from animal or plant material and typically comprise mostly triglycerides along with lesser amounts of free fatty acids and mono- or di-glycerides. In certain embodiments, the lipid is a plant-derived fat material that is solid or semi-solid at room temperature (i.e., at about 25° C.) and which at least partially liquefies when subjected to the temperature of the oral cavity of the user. The melting point of the lipid can vary and in certain embodiments may be within the range of about 36° C. to about 45° C. (e.g., about 38° C. to about 41° C.).

Plant-derived fats are comprised primarily of saturated or unsaturated fatty acid chains (most of which are bound within triglyceride structures) having a carbon length of about 10 to about 26 carbon atoms, more typically about 14 to about 20 carbon atoms, and most often about 14 to about 18 carbon atoms. Exemplary plant-derived fats that can be used include palm oil, palm kernel oil, soybean oil, cottonseed oil, and mixtures thereof. According to some aspects, the lipid substance may be hydrogenated, partially hydrogenated, or non-hydrogenated. In some instances, the lipid substance may include a blend of lipid components. For example, the lipid substance may include a blend of palm oil and palm kernel oil.

In certain specific embodiments, a meltable-type formulation is provided, which comprises a nicotinic compound, about 10 to about 50 percent lipid component, about 0 to about 1 percent artificial sweetener, about 20 to about 40 percent filler, a flavorant in an amount of up to about 10 percent, and salt in an amount up to about 5 percent, based on the total dry weight of the formulation. Specific lipids and greater detail regarding meltable-type formulations comprising lipids can be found in U.S. patent application Ser. No. 13/330,929, filed Dec. 20, 2011 to Cantrell et al., which is incorporated herein by reference.

A typical chewable-type formulation typically comprises a nicotinic compound, a natural gum (e.g., gum arabic), a lipid component, and an emulsifier. In one specific embodiment, the chewable-type formulation comprises gum arabic, an emulsifier, a lipid component, glycerin, a nicotinic compound, sucralose, sodium chloride, sodium hydroxide, and a flavorant.

A typical hard coating-type formulation typically comprises a nicotinic compound, a binder, and a sugar alcohol syrup. In one specific embodiment, the hard coating-type formulation comprises a nicotinic compound, a binder, a sugar alcohol, isomalt, sodium hydroxide, sucralose, and a flavorant. Although hard coating-type formulations according to the invention typically comprise such components, it is noted that other types of coatings can be applied in certain embodiments and may, in some embodiments, be applied in addition to the hard coating-type formulation. For example, the entire multi-layered pharmaceutical composition of the invention and/or any of the component formulations described herein may, in certain embodiments, include an outer coating, which may comprise ingredients such as carnauba wax and/or pharmaceutically acceptable forms of shellacs, glazing compositions and surface polish agents. Application of a coating can be accomplished using techniques such as airless spraying, fluidized bed coating, use of a coating pan, or the like. Other materials for use as a coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof. For example, such a coating can comprise a film-forming polymer, such as a cellulosic polymer, and an optional plasticizer. Other optional coating ingredients include flavorants, sweeteners, colorants, and salts.

A typical injection molded-type formulation (i.e., pastille) can comprise, for example, a nicotinic compound, and about 10 weight percent to about 25 weight percent of polysaccharide filler component on a dry weight basis. The polysaccharide filler can vary, but in certain embodiments, comprises polydextrose. Certain embodiments comprise one or more of a sugar alcohol filler (e.g., sorbitol), a binder comprising a water soluble gum (e.g., gum arabic), and/or components including flavorants, binders, emulsifiers, disintegration aids, humectants, and mixtures thereof. In one specific embodiment, the formulation comprises a nicotinic compound; at least about 10 dry weight percent of polysaccharide filler component; at least about 10 dry weight percent of at least one binder; at least about 20 dry weight percent of at least one humectant; and at least about 1 dry weight percent of at least one emulsifier. For more details on representative injection molded-type formulations, see U.S. patent application Ser. No. 12/957,838 to Cantrell et al., filed on Dec. 1, 2010, which is incorporated herein by reference.

A typical starch molded-type formulation (i.e., pastille) may comprise, for example, a nicotinic compound, at least one binder or gelling agent in the form of a natural gum, and at least one sugar alcohol as a filler component. In another embodiment, the starch molded-type formulation comprises a nicotinic compound, at least one binder or gelling agent in the form of a natural gum, sucrose, and corn syrup. For example, in one embodiment, a starch molded-type formulation comprises at least about 10 percent sugar alcohol filler, at least about 10 percent binder, about 0.1 to about 2 percent artificial sweetener, about 1 to about 5 percent humectant, about 1 to about 5 percent natural sweetener, up to about 5 percent flavorants, and up to about 3 percent salt, based on the total dry weight of the pharmaceutical composition.

One specific starch molded-type formulation comprises: at least about 10 dry weight percent of a sugar alcohol (e.g., sorbitol, isomalt, maltitol, and/or combinations thereof); at least about 10 or 15 dry weight percent of a natural gum binder component (e.g., gum arabic); at least about 0.5 dry weight percent of a humectant (e.g., glycerin); at least about 0.2 dry weight percent of a sweetener (e.g., sucralose); and at least about 0.5 dry weight percent of a flavorant. Another exemplary composition comprises: at least about 20 dry weight percent of a sugar alcohol; at least about 25 dry weight percent of a natural gum binder component; at least about 2 dry weight percent of a humectant; at least about 1 dry weight percent of a sweetener; and at least about 4 dry weight percent of a flavorant. In a still further embodiment, the composition comprises: at least about 30 dry weight percent of a sugar alcohol; at least about 40 dry weight percent of a natural gum binder component; at least about 2 dry weight percent of a humectant; and at least about 2 dry weight percent of a salt (e.g., NaCl). Yet another embodiment comprises: at least about 30 dry weight percent of sucrose; at least about 40 dry weight percent of a natural gum binder component; at least about 2 dry weight percent of a syrup (e.g., corn syrup); at least about 2 dry weight percent of a humectant; and at least about 2 dry weight percent of a salt. For more details on representative starch molded-type formulations, see U.S. application Ser. No. 12/957,821 to Cantrell et al., filed Dec. 1, 2010, which is incorporated herein by reference.

The formulations that make up the pharmaceutical composition of the present invention can have various organoleptic properties. For example, a starch molded-type formulation can, in certain embodiments, be characterized as dissolvable and lightly chewable and is generally in the form of a hardened solid gel (e.g., a "pastille"). In certain embodiments, starch molded-type formulations are characterized by sufficient cohesiveness to withstand light chewing action in the oral cavity without rapidly disintegrating. Such formulations of the disclosure typically do not exhibit a highly deformable chewing quality as found in conventional chewing gum. A meltable formulation can be, in certain embodiments, described as capable of providing a smooth and creamy sensation when in the mouth of the user (rather than a slick, waxy or slimy sensation). A lozenge-type formulation generally is hard in texture and exhibits a dissolvable quality. A chewable formulation generally exhibits a chewiness that is between that of a pastille as described herein and a gum. Like a pastille, a chewable formulation typically exhibits cohesiveness to withstand light chewing action in the oral cavity, but typically disintegrates at a slower rate than a pastille, allowing for more chewing action prior to complete disintegration of the composition. A hard coating-type formulation generally provides some sense of crunchiness or crispness.

The structure and makeup of the formulations within a given multi-layered pharmaceutical composition can vary. In certain embodiments, 2-component and 3-component pharmaceutical compositions are provided as shown in Table 1, where the Core may refer to the innermost component of a coated formulation and Layer 1 and Layer 2 are layers applied consecutively to the core formulation. The core may alternatively refer to one component of a side-by-side-type configuration, where Layer 1 is applied such that it is adhered to the Core formulation on at least one surface and Layer 2, where present, is adhered to the Layer 1 formulation on at least one surface.

Table 1 describes various combinations of formulations that may comprise multi-layered pharmaceutical compositions. Depending on the specific composition of each formulation, Table 1 represents exemplary products of the present invention having different combinations of different formulations. Each formulation provided in Table 1 is preferably a formulation having a specific composition as described herein.

TABLE 1

Representative Pharmaceutical Compositions

| Core formulation | Layer 1 formulation | Layer 2 formulation |
|---|---|---|
| Meltable-type | Lozenge-type | None |
| Meltable-type | Starch molded-type | None |
| Meltable-type | Injection molded-type | None |
| Meltable-type | Chewable-type | None |
| Meltable-type | Hard coating-type | None |
| Lozenge-type | Meltable-type | None |
| Lozenge-type | Starch molded-type | None |
| Lozenge-type | Injection molded-type | None |
| Lozenge-type | Chewable-type | None |
| Lozenge-type | Hard coating-type | None |
| Starch molded-type | Meltable-type | None |
| Starch molded-type | Lozenge-type | None |
| Starch molded-type | Injection molded-type | None |
| Starch molded-type | Chewable-type | None |
| Starch-molded type | Hard coating-type | None |
| Injection molded-type | Meltable-type | None |
| Injection molded-type | Lozenge-type | None |
| Injection molded-type | Starch molded-type | None |
| Injection molded-type | Chewable-type | None |
| Injection molded-type | Hard coating-type | None |
| Chewable-type | Lozenge-type | None |
| Chewable-type | Meltable-type | None |
| Chewable-type | Starch molded-type | None |
| Chewable-type | Injection molded-type | None |
| Chewable-type | Hard coating-type | None |
| Hard coating-type | Lozenge-type | None |
| Hard coating-type | Meltable-type | None |
| Hard coating-type | Starch molded-type | None |
| Hard coating-type | Injection molded-type | None |
| Hard coating-type | Chewable-type | None |
| Meltable-type | Lozenge-type | Meltable-type |
| Meltable-type | Lozenge-type | Injection molded-type |
| Meltable-type | Lozenge-type | Starch molded-type |
| Meltable-type | Lozenge-type | Chewable-type |
| Meltable-type | Lozenge-type | Hard coating-type |
| Meltable-type | Starch molded-type | Meltable-type |
| Meltable-type | Starch molded-type | Lozenge-type |
| Meltable-type | Starch molded-type | Injection molded-type |
| Meltable-type | Starch molded-type | Chewable-type |
| Meltable-type | Starch molded-type | Hard coating-type |
| Meltable-type | Injection molded-type | Meltable-type |
| Meltable-type | Injection molded-type | Lozenge-type |
| Meltable-type | Injection molded-type | Starch molded-type |
| Meltable-type | Injection molded-type | Chewable-type |
| Meltable-type | Injection molded-type | Hard coating-type |
| Meltable-type | Chewable-type | Meltable-type |
| Meltable-type | Chewable-type | Lozenge-type |
| Meltable-type | Chewable-type | Starch molded-type |
| Meltable-type | Chewable-type | Injection molded-type |
| Meltable-type | Chewable-type | Hard coating-type |
| Meltable-type | Hard coating-type | Meltable-type |
| Meltable-type | Hard coating-type | Lozenge-type |
| Meltable-type | Hard coating-type | Starch molded-type |
| Meltable-type | Hard coating-type | Injection molded-type |
| Meltable-type | Hard coating-type | Chewable-type |
| Lozenge-type | Meltable-type | Lozenge-type |
| Lozenge-type | Meltable-type | Starch molded-type |
| Lozenge-type | Meltable-type | Injection molded-type |
| Lozenge-type | Meltable-type | Chewable-type |
| Lozenge-type | Meltable-type | Hard coating-type |
| Lozenge-type | Starch molded-type | Meltable-type |
| Lozenge-type | Starch molded-type | Lozenge-type |
| Lozenge-type | Starch molded-type | Injection molded-type |
| Lozenge-type | Starch molded-type | Chewable-type |
| Lozenge-type | Starch molded-type | Hard coating-type |
| Lozenge-type | Injection molded-type | Lozenge-type |
| Lozenge-type | Injection molded-type | Meltable-type |
| Lozenge-type | Injection molded-type | Starch molded-type |
| Lozenge-type | Injection molded-type | Chewable-type |
| Lozenge-type | Injection molded-type | Hard coating-type |
| Lozenge-type | Chewable-type | Lozenge-type |
| Lozenge-type | Chewable-type | Meltable-type |
| Lozenge-type | Chewable-type | Injection molded-type |
| Lozenge-type | Chewable-type | Starch molded-type |
| Lozenge-type | Chewable-type | Hard coating-type |
| Lozenge-type | Hard coating-type | Lozenge-type |
| Lozenge-type | Hard coating-type | Meltable-type |
| Lozenge-type | Hard coating-type | Injection molded-type |
| Lozenge-type | Hard coating-type | Starch molded-type |
| Lozenge-type | Hard coating-type | Chewable-type |
| Starch molded-type | Meltable-type | Lozenge-type |
| Starch molded-type | Meltable-type | Injection molded-type |
| Starch molded-type | Meltable-type | Starch molded-type |
| Starch molded-type | Meltable-type | Chewable-type |
| Starch molded-type | Meltable-type | Hard coating-type |
| Starch molded-type | Lozenge-type | Meltable-type |
| Starch molded-type | Lozenge-type | Starch molded-type |
| Starch molded-type | Lozenge-type | Injection molded-type |
| Starch molded-type | Lozenge-type | Chewable-type |
| Starch molded-type | Lozenge-type | Hard coating-type |
| Starch molded-type | Injection molded-type | Meltable-type |
| Starch molded-type | Injection molded-type | Lozenge-type |
| Starch molded-type | Injection molded-type | Starch molded-type |
| Starch molded-type | Injection molded-type | Chewable-type |
| Starch molded-type | Injection molded-type | Hard coating-type |
| Starch molded-type | Chewable-type | Lozenge-type |
| Starch molded-type | Chewable-type | Meltable-type |
| Starch molded-type | Chewable-type | Starch molded-type |
| Starch molded-type | Chewable-type | Injection molded-type |
| Starch molded-type | Chewable-type | Hard coating-type |
| Starch molded-type | Hard coating-type | Lozenge-type |
| Starch molded-type | Hard coating-type | Meltable-type |
| Starch molded-type | Hard coating-type | Starch molded-type |
| Starch molded-type | Hard coating-type | Injection molded-type |
| Starch molded-type | Hard coating-type | Chewable-type |
| Injection molded-type | Meltable-type | Lozenge-type |
| Injection molded-type | Meltable-type | Injection molded-type |
| Injection molded-type | Meltable-type | Starch molded-type |
| Injection molded-type | Meltable-type | Chewable-type |
| Injection molded-type | Meltable-type | Hard coating-type |
| Injection molded-type | Lozenge-type | Meltable-type |
| Injection molded-type | Lozenge-type | Injection molded-type |
| Injection molded-type | Lozenge-type | Starch molded-type |
| Injection molded-type | Lozenge-type | Chewable-type |
| Injection molded-type | Lozenge-type | Hard coating-type |
| Injection molded-type | Starch molded-type | Lozenge-type |
| Injection molded-type | Starch molded-type | Meltable-type |
| Injection molded-type | Starch molded-type | Injection molded-type |
| Injection molded-type | Starch molded-type | Chewable-type |
| Injection molded-type | Starch molded-type | Hard coating-type |
| Injection molded-type | Chewable-type | Lozenge-type |
| Injection molded-type | Chewable-type | Meltable-type |
| Injection molded-type | Chewable-type | Starch molded-type |
| Injection molded-type | Chewable-type | Injection molded-type |
| Injection molded-type | Chewable-type | Hard coating-type |
| Injection molded-type | Hard coating-type | Lozenge-type |
| Injection molded-type | Hard coating-type | Meltable-type |
| Injection molded-type | Hard coating-type | Starch molded-type |
| Injection molded-type | Hard coating-type | Injection molded-type |
| Injection molded-type | Hard coating-type | Chewable-type |
| Chewable-type | Lozenge-type | Meltable-type |
| Chewable-type | Lozenge-type | Starch molded-type |
| Chewable-type | Lozenge-type | Injection molded-type |
| Chewable-type | Lozenge-type | Chewable-type |
| Chewable-type | Lozenge-type | Hard coating-type |
| Chewable-type | Meltable-type | Lozenge-type |
| Chewable-type | Meltable-type | Starch molded-type |
| Chewable-type | Meltable-type | Injection molded-type |
| Chewable-type | Meltable-type | Chewable-type |
| Chewable-type | Meltable-type | Hard coating-type |
| Chewable-type | Starch molded-type | Lozenge-type |
| Chewable-type | Starch molded-type | Meltable-type |
| Chewable-type | Starch molded-type | Injection molded-type |
| Chewable-type | Starch molded-type | Chewable-type |
| Chewable-type | Starch molded-type | Hard coating-type |
| Chewable-type | Injection molded-type | Lozenge-type |
| Chewable-type | Injection molded-type | Meltable-type |

TABLE 1-continued

Representative Pharmaceutical Compositions

| Core formulation | Layer 1 formulation | Layer 2 formulation |
| --- | --- | --- |
| Chewable-type | Injection molded-type | Starch molded-type |
| Chewable-type | Injection molded-type | Chewable-type |
| Chewable-type | Injection molded-type | Hard coating-type |
| Chewable-type | Hard coating-type | Lozenge-type |
| Chewable-type | Hard coating-type | Meltable-type |
| Chewable-type | Hard coating-type | Starch molded-type |
| Chewable-type | Hard coating-type | Injection molded-type |
| Chewable-type | Hard coating-type | Chewable-type |
| Hard coating-type | Lozenge-type | Meltable-type |
| Hard coating-type | Lozenge-type | Starch molded-type |
| Hard coating-type | Lozenge-type | Injection molded-type |
| Hard coating-type | Lozenge-type | Chewable-type |
| Hard coating-type | Lozenge-type | Hard coating-type |
| Hard coating-type | Meltable-type | Lozenge-type |
| Hard coating-type | Meltable-type | Starch molded-type |
| Hard coating-type | Meltable-type | Injection molded-type |
| Hard coating-type | Meltable-type | Chewable-type |
| Hard coating-type | Meltable-type | Hard coating-type |
| Hard coating-type | Starch molded-type | Lozenge-type |
| Hard coating-type | Starch molded-type | Meltable-type |
| Hard coating-type | Starch molded-type | Injection molded-type |
| Hard coating-type | Starch molded-type | Chewable-type |
| Hard coating-type | Starch molded-type | Hard coating-type |
| Hard coating-type | Injection molded-type | Lozenge-type |
| Hard coating-type | Injection molded-type | Meltable-type |
| Hard coating-type | Injection molded-type | Starch molded-type |
| Hard coating-type | Injection molded-type | Chewable-type |
| Hard coating-type | Injection molded-type | Hard coating-type |
| Hard coating-type | Chewable-type | Lozenge-type |
| Hard coating-type | Chewable-type | Meltable-type |
| Hard coating-type | Chewable-type | Starch molded-type |
| Hard coating-type | Chewable-type | Injection molded-type |
| Hard coating-type | Chewable-type | Hard coating-type |

Pharmaceutical compositions according to the present invention are advantageous in that they are capable of exhibiting various mixtures of organoleptic properties. In certain embodiments, because such pharmaceutical compositions are multi-layered, they can provide the user with a range of organoleptic sensations during use of the product. For example, pharmaceutical compositions can be tailored to exhibit a certain range of organoleptic properties in a desired order of experience (e.g., an initial hard, dissolvable sensation followed by a chewy sensation).

Due to the multi-layered structure of the pharmaceutical compositions of the present invention, it is possible in certain embodiments to tailor the flavor and/or nicotine release profile of the product as a whole. In other words, the manner and/or rate at which the nicotine released can vary. Certain types of formulations typically exhibit faster or slower release of nicotine. Such formulations can advantageously be positioned within the multi-layered structure of the pharmaceutical composition such that the product exhibits a desired release profile. For example, in one specific embodiment, the exterior formulation comprises a formulation that exhibits relatively fast release of nicotine, whereas the one or more internal formulations exhibit a more extended nicotine release profile, providing a product that provides both a fast initial release of nicotine and an extended release of nicotine. In certain embodiments, different flavorants and/or other components (e.g., sensates) can be incorporated within certain layers. Varying the flavors and/or organoleptic sensations of the different layers can provide the user with a unique range of taste and/or sensory experiences over the course of use of the product.

Compositions of the present invention incorporate a pharmaceutically effective amount of nicotine. The dose of active ingredient (i.e., all the various nicotine forms) is preferably that amount effective to treat some symptoms of, or prevent occurrence of the symptoms of, the condition, disease, or disorder from which the subject or patient suffers. By "effective amount", "therapeutic amount" or "effective dose" is meant that amount sufficient to elicit the desired pharmacological or therapeutic effects, thus resulting in effective prevention or treatment of the condition, disease, or disorder. Thus, an effective amount of active ingredient is an amount sufficient to enter relevant regions of the body (e.g., to pass across the blood-brain barrier of the subject), to bind to relevant receptor sites in the CNS and PNS of the subject, and/or to elicit neuropharmacological effects (e.g., elicit neurotransmitter secretion, thus resulting in effective prevention or treatment of the condition, disease, or disorder). Prevention of the disorder is manifested, for example, by delaying the onset of the symptoms of the condition, disease, or disorder. Treatment of the disorder is manifested by, for example, a decrease in the symptoms associated with the condition, disease, or disorder or an amelioration of the reoccurrence of the symptoms thereof.

For compositions of the present invention, the intended daily dose of the active ingredient can vary. The overall dose of active ingredient can depend upon factors such as the weight of the subject ingesting the composition, the condition being treated, the state or severity of the disease or disorder being treated, the desired pharmacological effect, or other such factors. Typically, the amount of nicotine active ingredient, calculated as nicotine base, administered to a subject per day is at least about 2 mg, often is at least about 4 mg, and frequently is at least about 10 mg. Typically, the amount of nicotine active ingredient administered to a subject per day does not exceed about 60 mg, often does not exceed about 50 mg, and frequently does not exceed about 40 mg. See also, for example, the types of dosing regimens and administration techniques set forth in U.S. Pat. No. 5,593,684 to Baker et al.; U.S. Pat. No. 6,660,754 to Kyle et al.; and US Pat. Pub. Nos. 2004/0006113 to Sachs; 2005/0214229 to Pinney et al.; 2008/0124283 to Andersen; and 2009/0293895 to Axelsson et al.; which are incorporated herein by reference.

Representative compositions incorporating nicotine as an active ingredient can have various types of formats and configurations, and as a result, the character, nature, behavior, consistency, shape, form, size and weight of the composition can vary. The shape of a representative composition can be generally spherical, cylindrical (e.g., ranging form the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, capsule, caplet, pouch and gum types of products that traditionally have been employed for the administration of pharmaceutical types of products. The general nature of a representative composition can be soft or hard to the touch, or of intermediate softness or hardness; and as such, the composition can be considered to be malleable, flexible, chewy, resilient, brittle, or the like. When administered orally, various components of the product can be considered to be readily dispersible or slow to disperse, or those various components can dissolve at varying rates (e.g., from relatively fast to relatively slow). As a result, for compositions ingested by insertion in the mouth of the human subject, the release rate of active ingredient during use of the product can vary from relatively fast to relatively slow, depending upon factors such as the design of the product and the use of product by the subject using that product. See also, by way of example, the types of products proposed in U.S. Pat. No. 4,655,231 to Ray et al.; U.S. Pat. No. 5,147,654 to Place et al.; U.S. Pat. No. 5,543,424 to Carlsson et al.; U.S. Pat. No. 6,268,386 to Thompson; U.S. Pat. No. 6,319,510 to Yates; U.S. Pat. No. 6,488,953 Halliday et al.; U.S. Pat. No. 6,709,671 to Zerbe et al.; U.S. Pat. No. 7,025,983 to Leung et al.; U.S. Pat. No. 7,105,173 to Rolling; U.S. Pat. No. 7,115,297 to Stillman; U.S. Pat. No. 7,435,749 to Knight; and U.S. Pat. No. 7,491,406 to Leung et al.; and US Pat. Pub. Nos. 2006/0198873 to Chan et al.; 2006/0240087 to Houze et al.; 2006/0204559 to Bess et al.; 2007/0269492 to Steen et al.; 2008/0020050 to Chau et al.; 2008/0286340 to Andersson et al.; 2008/0292683 to Sanghvi et al.; and 2009/0004248 to Bunick et al.; which are incorporated herein by reference.

The means by which multi-layered nicotinic compound-containing pharmaceutical compositions can be produced can vary. Generally, the core formulation can be provided by any means for providing such a formulation. Exemplary means for providing certain types of formulations are provided herein, although it is noted that other methods can be used without departing from the present invention. Typically, the core formulation is produced and the one or more additional layers are applied thereto. The core can be formed, for example, into the desired shape by pouring the formulation mixture directly into molds, forming (e.g., rolling or pressing) into the desired shape, or extruding. In some embodiments, the mixture can be extruded, starch molded, or injection molded.

In certain embodiments, the method by which the one or more additional layers are formed may require some degree of tailoring so as to accommodate application of the formulation onto the core or previous layer of the pharmaceutical composition. For example, second and subsequent layers of the pharmaceutical compositions are often applied by means of coatings (e.g., by dip coating, spray coating, or preparing a separate sheet of the formulation that can be used to enwrap the core formulation or to adhere to one or more surface of the core formulation, as in a side-by-side type configuration).

Typical conditions associated with manufacture of food grade products such as described herein include control of heat and temperature (i.e., the degree of heat to which the various ingredients are exposed during manufacture and the temperature of the manufacturing environment), moisture content (e.g., the degree of moisture present within individual ingredients and within the final composition), humidity within the manufacturing environment, atmospheric control (e.g., nitrogen atmosphere), airflow experienced by the various ingredients during the manufacturing process, and other similar types of factors. Additionally, various process steps involved in product manufacture can involve selection of certain solvents and processing aids, use of heat and radiation, refrigeration and cryogenic conditions, ingredient mixing rates, and the like. The manufacturing conditions also can be controlled due to selection of the form of various ingredients (e.g., solid, liquid, or gas), particle size or crystalline nature of ingredients of solid form, concentration of ingredients in liquid form, or the like. Ingredients can be processed into the desired composition by techniques such as extrusion, compression, spraying, and the like.

Meltable-type formulations can, in certain embodiments, be prepared by combining the components (e.g., a nicotinic compound and one or more additional components) with a melted lipid, and forming a molten pharmaceutical formulation slurry, which can then be deposited into a mold or coated onto another formulation.

Lozenge-type formulations may, in certain embodiments, be prepared by heating a mixture of ingredients comprising a high percentage of isomalt to about 143° C. Once all components are dissolved, the temperature is raised past the hard crack stage (e.g., to about 166° C.) and then removed from the heat to allow the mixture to cool. Various components can be added at certain stages (e.g., they may be added to the isomalt mixture at room temperature, may be added when the mixture reaches 143° C. or 166° C. or may be added at a given temperature during the cooling process).

Injection molded-type formulations can, in certain embodiments, be prepared by mixing the components (e.g., a nicotinic compound, binder, and polysaccharide filler component) to form a pharmaceutical formulation mixture; injection molding the pharmaceutical formulation mixture (e.g., by compressing the mixture using a compressive force of at least about 75,000 kPa or at least about 100,000 kPa); and cooling the pharmaceutical formulation mixture to form a solidified pharmaceutical formulation (e.g., cooling to a temperature of about 20° C. to about 25° C.).

The means by which the formulations are prepared can vary and certain methods of making certain formulation types may have to be adapted, depending upon the makeup of a given pharmaceutical composition. For example, where an outer layer comprises a formulation that is traditionally molded, the method may require modification such that that the formulation can be coated onto another formulation. For example, such formulations can be capable of being wet- or dry-sprayed onto another surface or applied to another surface by dipping that surface into the formulation. Depending on the nature of the formulation, the method of application may require modification of traditional spray coating techniques. For example, to spray coat a lozenge-type formulation onto another formulation, it may be necessary to maintain the formulation and the spray coating equipment at an elevated temperature during the process. In certain embodiments, temperature control is important to avoid altering the nature of other formulations. For example, care must be taken to avoid melting a meltable-type formulation in the core of a pharmaceutical composition during the application of an additional layer.

In certain embodiments, at least a portion of the pharmaceutical composition is transparent or translucent as defined herein. Transparency/translucency can be determined by any means commonly used in the art; however, it is commonly measured by spectrophotometric light transmission over a range of wavelengths (e.g., from about 400-700 nm). Transmission measurements for certain pharmaceutical compositions of the present invention may be higher than those of traditional nicotine-containing pharmaceutical compositions. Translucency can also be confirmed by visual inspection by simply holding the pharmaceutical composition up to a light source and determining if light travels through the product in a diffuse manner.

Aspects of the present invention are more fully illustrated by the following examples, which are set forth to illustrate certain aspects of the present invention and are not to be construed as limiting thereof.

EXPERIMENTAL

Example 1

Preparation of Lozenge-type Formulations

A nicotinic compound-containing formulation suitable for use as a lozenge-type component of a pharmaceutical composition for oral use is provided in the following manner. Isomalt, NaCl, and vanillin are mixed in a pot and the temperature of the mixture is brought to 143° C. The mixture is held at 143° C. until the isomalt is melted and the temperature is then increased to 166° C. In a separate vessel, nicotine, maltitol syrup, $H_2O$, sucralose, and, optionally, L-lysine are mixed to form a solution. Optionally, in a second separate vessel, water and sodium hydroxide are mixed to form a solution.

The isomalt mixture is removed from the heat and allowed to cool to 132° C. The remaining components (i.e., the nicotine-containing solution and optional sodium hydroxide solution) are combined and, optionally, one or more flavorings are added to the combined solution. The combined solution is poured into the hot isomalt mixture and folded in.

The resulting mixture is poured into molds. When the mixture becomes too viscous to pour, the mixture can be heated in a microwave using high heat (e.g., for about 7 seconds). Representative pharmaceutical formulation mixtures are set forth below. Mixture 1 below contains no base, while Mixtures 2 and 3 contain sodium hydroxide at varying levels.

| MIXTURE 1 | |
|---|---|
| Ingredient | Percent by weight |
| Isomalt ST-M* | 93.8 |
| Maltitol syrup | 1.0 |
| Nicotine | 0.2 |
| NaCl | 1.0 |
| Vanillin | 0.3 |
| Sucralose | 0.2 |
| $H_2O$ | 3.3 |
| Flavorant | 0.1 |

*Isomalt in which 1,6-GPS and 1,1-GPM are present in essentially equimolar amounts and which has a medium grain size, the diameter of approximately 90% of all particles being <3 mm.

| Ingredient | Percent by weight |
|---|---|
| MIXTURE 2 | |
| Isomalt ST-M | 93.8 |
| Maltitol syrup | 1.0 |
| Nicotine | 0.2 |
| NaCl | 1.0 |
| Vanillin | 0.3 |
| Sucralose | 0.2 |
| $H_2O$ | 3.1 |
| Flavorant | 0.1 |
| NaOH | 0.2 |
| MIXTURE 3 | |
| Isomalt ST-M | 94.2 |
| Maltitol syrup | 1.0 |
| Nicotine | 0.2 |
| NaCl | 1.0 |
| Vanillin | 0.3 |
| Sucralose | 0.2 |
| $H_2O$ | 2.7 |
| Flavorant | 0.1 |
| NaOH | 0.3 |

Other acceptable excipients of lozenge-type formulations are provided, for example, in U.S. patent application Ser. No. 13/240,500 to Holton, Jr. filed on Sep. 22, 2011, which is incorporated herein by reference.

Example 2

Preparation of Meltable-type Formulations a) Meltable Formulation 1

A nicotinic compound-containing formulation suitable for use as a meltable component of a pharmaceutical composition for oral use is provided in the following manner. Various dry ingredients are provided, which include a filler (isomalt), a salt (sodium chloride), a sweetener (sucralose), and flavorants (vanillin, spray-dried peppermint, spray-dried menthol). All dry ingredients, in powder form, as well as a nicotinic compound (e.g., nicotine), are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing a blend of palm kernel oil and palm oil. The lipid substance is melted in a mixing vessel. While maintaining heat to the mixing vessel having the melted lipid substance, the mixed dry formulation is added while mixing occurs, thereby creating a flowable slurry of a nicotinic compound-containing composition having a moisture content of less than about 10 percent. The slurry is deposited in a mold to achieve about 1 gram weight per piece of pharmaceutical composition. The slurry is allowed to harden by ambient air drying for about 45 minutes, after which the individual pieces of meltable nicotinic compound-containing formulation are removed from the mold. The mixture of the nicotinic compound-containing composition is about 53.0 parts lipid substance, 39.8 parts filler, 0.2 parts nicotine, 0.8 parts salt, 0.7 parts sweetener, and 5.5 parts flavorant.

b) Meltable Formulation 2

A nicotinic compound-containing formulation suitable for use as a meltable component of a pharmaceutical composition for oral use is provided in the following manner. Various dry ingredients are provided, which include a filler (isomalt), a salt (sodium chloride), a sweetener (sucralose), and flavorants (vanillin, spray-dried peppermint, spray-dried menthol). All dry ingredients, in powder form, as well as a nicotinic compound (e.g., nicotine), are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing a blend of palm kernel oil and palm oil. The lipid substance is melted in a mixing vessel. While maintaining heat to the mixing vessel having the melted lipid substance, the mixed dry formulation is added while mixing occurs, thereby creating a flowable slurry of nicotinic compound-containing composition having a moisture content of less than about 10 percent. The slurry is deposited in a mold to achieve about 1 gram weight per piece of pharmaceutical composition. The slurry is allowed to harden by ambient air drying for about 45 minutes, after which the individual pieces of meltable nicotinic compound-containing formulation are removed from the mold. The mixture of the nicotinic compound-containing composition is about 53.0 parts lipid substance, 38.2 parts filler, 0.2 parts nicotine, 0.8 parts salt, 0.7 parts sweetener, and 7.1 parts flavorant.

c) Meltable Formulation 3

A nicotinic compound-containing formulation suitable for use as a meltable component of a pharmaceutical composition for oral use is provided in the following manner. Various dry ingredients are provided, which include a filler (isomalt), a salt (sodium chloride), a sweetener (sucralose), and flavorants (vanillin, spray-dried peppermint, spray-dried menthol). All dry ingredients, in powder form, as well as a nicotinic compound (e.g., nicotine), are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing a blend of palm kernel oil and palm oil. The lipid substance is melted in a mixing vessel. While maintaining heat to the mixing vessel having the melted lipid substance, the mixed dry formulation is added while mixing occurs, thereby creating a flowable slurry of nicotinic compound-containing composition having a moisture content of less than about 10 percent. The slurry is deposited in a mold to achieve about 1 gram weight per piece of nicotinic compound-containing formulation. The slurry is allowed to harden by ambient air drying for about 45 minutes, after which the individual pieces of meltable nicotinic compound-containing formulation are removed from the mold. The mixture of the nicotinic compound-containing composition is about 53.0 parts lipid substance, 36.6 parts filler, 0.2 parts nicotine, 0.8 parts salt, 0.7 parts sweetener, and 8.7 parts flavorant.

d) Meltable Formulation 4

A nicotinic compound-containing formulation suitable for use as a meltable component of a pharmaceutical composition for oral use is provided in the following manner. Various dry ingredients are provided, which include a filler (isomalt), a sweetener (sucralose), and a flavorant (vanillin). All dry ingredients, in powder form, as well as a nicotinic compound (e.g., nicotine), are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing palm kernel oil and palm oil. The lipid substance is melted in a mixing vessel. While maintaining heat to the mixing vessel having the melted lipid substance, the mixed dry formulation is added while mixing occurs, thereby creating a flowable slurry of nicotinic compound-containing composition having a moisture content of less than about 10 percent. The slurry is deposited in a mold to achieve about 1 gram weight per piece of nicotinic compound-containing formulation. The slurry is allowed to harden by ambient air drying for about 45 minutes, after which the individual pieces of nicotinic compound-containing formulation are removed from the mold. The mixture of the nicotinic compound-containing composition is about 52.9 parts lipid substance, 46.1 parts filler, 0.2 parts nicotine, 0.7 parts sweetener, and 0.1 parts flavorant.

e) Meltable Formulation 5

A nicotinic compound-containing formulation suitable for use as a meltable component of a pharmaceutical composition for oral use is provided in the following manner. Various dry ingredients are provided, which include a filler (isomalt), additives (sodium chloride, flour), a sweetener (sucralose), and a flavorant (vanillin). All dry ingredients, in powder form, as well as a nicotinic compound (e.g., nicotine), are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing palm kernel oil and palm oil. The lipid substance is melted in a mixing vessel. While maintaining heat to the mixing vessel having the melted lipid substance, the mixed dry formulation is added while mixing occurs, thereby creating a flowable slurry of nicotinic compound-containing composition having a moisture content of less than about 10 percent. The slurry is deposited in a mold to achieve about 1 gram weight per piece of nicotinic compound-containing formulation. The slurry is allowed to harden by ambient air drying for about 45 minutes, after which the individual pieces of nicotinic compound-containing formulation are removed from the mold. The mixture of the nicotinic compound-containing composition is about 53.0 parts lipid substance, 45.2 parts filler, 0.2 parts nicotine, 0.8 parts additive, 0.7 parts sweetener, and 0.1 parts flavorant.

f) Meltable Formulation 6

A nicotinic compound-containing formulation suitable for use as a meltable component of a pharmaceutical composition for oral use is provided in the following manner. Various dry ingredients are provided, which include a filler (isomalt), additives (sodium chloride, flour), a sweetener (sucralose), and a flavorant (vanillin). All dry ingredients, in powder form, as well as a nicotinic compound (e.g., nicotine), are added together and thoroughly mixed in a Hobart mixer with a paddle for about three minutes at about 120 rpm.

A lipid substance having a melting point of about 39° C. to about 41° C. is provided (available as 108-48-B from AarhusKarlshamn USA Inc.). The lipid substance is non-hydrogenated lauric coating fat containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of nicotinic compound-containing composition having a moisture content of less than about 10 percent. The slurry is deposited in a mold to achieve about 1 gram weight per piece of pharmaceutical composition. The slurry is allowed to harden by ambient air drying for about 45 minutes, after which the individual pieces of nicotinic compound-containing composition are removed from the mold. The mixture of the nicotinic compound-containing composition is about 53.0 parts lipid substance, 45.2 parts filler, 0.2 parts nicotine, 0.8 parts additive, 0.7 parts sweetener, and 0.1 parts flavorant.

g) Meltable Formulation 7

A nicotinic compound-containing formulation suitable for use as a meltable component of a pharmaceutical composition for oral use is provided in the following manner. Various dry ingredients are provided, which include a filler (isomalt), a salt (sodium chloride), a sweetener (sucralose), and two flavorants (vanillin and mint) All dry ingredients, in powder form, as well as a nicotinic compound (e.g., nicotine), are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing palm kernel oil and palm oil. The lipid substance is melted in a mixing vessel using a microwave. The melted lipid is slowly added to the dry blend while stirring. While maintaining heat to the mixing vessel, addition of the entire melted lipid component creates a flowable slurry of nicotinic compound-containing composition. The slurry is deposited in a mold to achieve about 1 gram weight per piece nicotinic compound-containing composition. The slurry is allowed to harden by ambient air drying for about 45 minutes, after which the individual pieces of nicotinic compound-containing formulation are removed from the mold. The mixture of the nicotinic compound-containing composition is about 53.0 parts lipid substance, 45.2 parts filler, 0.2 parts nicotine, 0.8 parts additive, 0.7 parts sweetener, and 0.1 parts flavorant.

Other acceptable excipients of meltable-type formulations are provided, for example, in U.S. patent application Ser. No. 13/330,929, filed Dec. 20, 2011 to Cantrell et al., which is incorporated herein by reference.

Example 3

Preparation of Starch Molded-type Formulations (Pastilles)

a) Starch Molded Formulation 1

A nicotinic compound-containing formulation suitable for use as a starch molded component of a pharmaceutical composition for oral use is provided in the following manner. An aqueous mixture is prepared. The aqueous mixture is formed by hydrating a binder material (gum arabic) with water and then admixing the hydrated gum with a filler (isomalt), an additional filler (maltitol; available as LYCASIN from Roquette Frères S.A.), and a salt using a high shear mixer. The aqueous mixture is about 33 parts binder material, 29 parts isomalt, 4.1 parts maltitol, 2 parts salt, and 33 parts water.

The aqueous mixture is mixed with a sweetener (sucralose) and nicotine in a Hobart mixing bowl to form a nicotinic compound-containing composition. The mixture of the nicotinic compound-containing composition is about 99.3 parts aqueous mixture, 0.2 parts nicotine, and 0.5 parts sucralose.

The nicotinic compound-containing composition is heated to about 54° C. and then deposited into a starch mould. The nicotinic compound-containing composition remains in the starch mould for about 19 hours at about 60° C. The nicotinic compound-containing composition is allowed to cool and then removed from the starch mould. The nicotinic compound-containing composition is then cured at ambient room temperature for about 24 hours.

b) Starch Molded Formulation 2

A nicotinic compound-containing formulation suitable for use as a starch molded component of a pharmaceutical composition for oral use is provided in the following manner. An aqueous mixture is prepared by hydrating a binder material (gum arabic) with water and adding sodium hydroxide to adjust the mixture to a pH of 8.0. The mixture is heated to about 82° C. Separately, isomalt and maltitol syrup are combined and heated to about 166° C., cooled to about 132° C., and added to the aqueous mixture. Flavorant, salt, sucralose, glycerin, and nicotine are added and mixed. The mixture of the nicotinic compound-containing composition is about 64.2 parts aqueous mixture (32 parts water, 32 parts binder, 0.2 parts buffering agent), 0.2 parts nicotine, 2.4 parts glycerin, 29.0 parts isomalt, 1.3 parts maltitol syrup, 0.3 parts sucralose, 2 parts salt, 0.6 parts flavorant.

The nicotinic compound-containing composition deposited into a starch mould at a temperature of about 71° C. (depositing temperature should be greater than about 66° C.). The nicotinic compound-containing composition remains in the starch mould for about 72 hours at about 60° C. The nicotinic compound-containing composition is allowed to cool and then removed from the starch mould. The nicotinic compound-containing composition is then cured at ambient room temperature for about 24 hours.

Other acceptable excipients of starch molded-type formulations are provided, for example, in U.S. application Ser. No. 12/957,821 to Cantrell et al., filed Dec. 1, 2010, which is incorporated herein by reference.

Example 4

Preparation of Injection Molded-type Formulations (Pastilles)

a) Injection Molded Formulation 1

A nicotinic compound-containing formulation suitable for use as an injection molded component of a pharmaceutical composition for oral use is provided in the following manner. A humectant (available as HYSTAR 3375 from Corn Products International), an emulsifier (available as DUR-EM 117 from Loders Croklaan), corn syrup, glycerin and a flavorant are admixed and heated to form a liquid blend.

Nicotine is mixed with salt, sucralose, a binder material (gum arabic) and polydextrose powder (available as LITESSE from Danisco A/S) in a Hobart mixing bowl. The liquid blend is added to the Hobart mixing bowl containing the nicotine blend, binder material, and polydextrose powder, wherein the ingredients are admixed in Hobart mixer (Model N-50) for about 4-5 minutes at about 120 rpm to form a nicotinic compound-containing composition. The nicotinic compound-containing composition is passed through a meat grinder on the Hobart mixer to incorporate the liquid ingredients into the dry ingredients. The nicotinic compound-containing composition is extruded through a grinder apparatus. Upon extrusion, the nicotinic compound-containing composition is placed in a Hobart mixer to form a powder granulation. The mixture of the nicotinic compound-containing composition is about 21.4 parts binder material, 0.2 parts nicotine, 42.7 parts humectant, 1.5 part emulsifier, 21.4 parts polydextrose, 5.3 parts corn syrup, 3.2 parts glycerin, 2.8 parts salt, 0.3 parts sucralose, and 1.2 parts flavorant.

The granulated nicotinic compound-containing composition is transferred to an injection mold and compressed at about 103,500 kPa for 1 minute. The mold is a stainless steel two-piece block that is filled with the nicotinic compound-containing composition and then compressed via engagement with a hydraulic press unit (Wabach Hydraulic Press, Model 12-102T, Serial 2201). The nicotinic compound-containing composition is removed from the injection mold after cooling at ambient temperature for about 60 minutes.

b) Injection Molded Formulation 2

A nicotinic compound-containing composition suitable for use as a pharmaceutical composition for oral use is provided in the following manner. A filler (maltitol; available as LYCASIN from Roquette Frères S.A.), an emulsifier (available as DUR-EM 117 from Loders Croklaan), corn syrup, glycerin and a flavorant are admixed and heated to form a liquid blend.

Nicotine is mixed with salt, sucralose, a binder material (gum arabic) and a polysaccharide (maltodextrin; available as MALTRIN M100 from Grain Processing Corporation) in a Hobart mixing bowl. The liquid blend is added to the Hobart mixing bowl containing the nicotine blend, binder material, and polysaccharide, wherein the ingredients are admixed in Hobart mixer (Model N-50) for about 4-5 minutes at about 120 rpm to form a nicotinic compound-containing composition. The nicotinic compound-containing composition is passed through a meat grinder on the Hobart mixer to incorporate the liquid ingredients into the dry ingredients. The nicotinic compound-containing composition is extruded through a grinder apparatus. Upon extrusion, the nicotinic compound-containing composition is placed in a Hobart mixer to form a powder granulation. The mixture of the nicotinic compound-containing composition is about 21.4 parts binder material, 0.2 parts nicotine, 21.4 parts polysaccharide, 42.7 parts filler, 1.5 parts emulsifier, 5.3 parts corn syrup, 3.2 parts glycerin, 2.9 parts salt, 0.3 parts sucralose, and 1.2 parts flavorant.

The granulated nicotinic compound-containing composition is transferred to an injection mold and compressed at about 103,500 kPa for 1 minute. The mold is a stainless steel two-piece block that is filled with the nicotinic compound-containing composition and then compressed via engagement with a hydraulic press unit (Wabach Hydraulic Press, Model 12-102T, Serial 2201). The nicotinic compound-containing composition is removed from the injection mold after cooling at ambient temperature for about 60 minutes.

c) Injection Molded Formulation 3

A nicotinic compound-containing composition suitable for use as a pharmaceutical composition for oral use is provided in the following manner. A filler (maltitol; available as LYCASIN from Roquette Frères S.A.), an emulsifier (available as DUR-EM 117 from Loders Croklaan), corn syrup, glycerin and a flavorant are admixed and heated to form a liquid blend.

Nicotine is mixed with salt, sucralose, a binder material (gum arabic) and a polysaccharide (pullulan powder) in a Hobart mixing bowl. The liquid blend is added to the Hobart mixing bowl containing the nicotine blend, binder material, and polysaccharide, wherein the ingredients are admixed in Hobart mixer (Model N-50) for about 4-5 minutes at about 120 rpm to form a nicotinic compound-containing composition. The nicotinic compound-containing composition is passed through a meat grinder on the Hobart mixer to incorporate the liquid ingredients into the dry ingredients. The nicotinic compound-containing composition is extruded through a grinder apparatus. Upon extrusion, the nicotinic compound-containing composition is placed in a Hobart mixer to form a powder granulation. The mixture of the nicotinic compound-containing composition is about 21.4 parts binder material, 0.2 parts nicotine, 21.4 parts polysaccharide, 42.6 parts filler, 1.5 parts emulsifier, 5.3 parts corn syrup, 3.2 parts glycerin, 2.8 parts salt, 0.3 parts sucralose, and 1.3 parts flavorant.

The granulated nicotinic compound-containing composition is transferred to an injection mold and compressed at about 103,500 kPa for 1 minute. The mold is a stainless steel two-piece block that is filled with the nicotinic compound-containing composition and then compressed via engagement with a hydraulic press unit (Wabach Hydraulic Press, Model 12-102T, Serial 2201). The nicotinic compound-containing composition is removed from the injection mold after cooling at ambient temperature for about 60 minutes.

d) Injection Molded Formulation 4

A nicotinic compound-containing composition suitable for use as a pharmaceutical composition for oral use is provided in the following manner. A humectant (available as HYSTAR 3375 from Corn Products International), an emulsifier (available as DUR-EM 117 from Loders Croklaan), corn syrup, glycerin and a flavorant are admixed and heated to form a liquid blend.

Nicotine is mixed with salt, sucralose, a binder material (gum arabic) and polydextrose powder (available as LITESSE from Danisco AIS) in a Hobart mixing bowl. The liquid blend is added to the Hobart mixing bowl containing the nicotine blend, binder material, and polydextrose powder, wherein the ingredients are admixed in Hobart mixer (Model N-50) for about 4-5 minutes at about 120 rpm to form a nicotinic compound-containing composition. The nicotinic compound-containing composition is passed through a meat grinder on the Hobart mixer to incorporate the liquid ingredients into the dry ingredients. The nicotinic compound-containing composition is extruded through a grinder apparatus. Upon extrusion, the nicotinic compound-containing composition is placed in a Hobart mixer to form a powder granulation. The mixture of the nicotinic compound-containing composition is about 22.4 parts binder material, 0.2 parts nicotine, 40 parts humectant, 1.6 parts emulsifier, 22.4 parts polydextrose, 5.6 parts corn syrup, 3.4 parts glycerin, 2.8 parts salt, 0.3 parts sucralose, and 1.3 parts flavorant.

The granulated nicotinic compound-containing composition is transferred to an injection mold and compressed at about 103,500 kPa for 1 minute. The mold is a stainless steel two-piece block that is filled with the nicotinic compound-containing composition and then compressed via engagement with a hydraulic press unit (Wabach Hydraulic Press, Model 12-102T, Serial 2201). The nicotinic compound-containing composition is removed from the injection mold after cooling at ambient temperature for about 60 minutes.

e) Injection Molded Formulation 5

A nicotinic compound-containing composition suitable for use as a pharmaceutical composition for oral use is provided in the following manner. A humectant (available as HYSTAR 3375 from Corn Products International), an emulsifier (available as DUR-EM 117 from Loders Croklaan), corn syrup, glycerin and a flavorant are admixed and heated to form a liquid blend.

Nicotine is mixed with salt, sucralose, a binder material (gum arabic) and polydextrose powder (available as LITESSE from Danisco A/S) in a Hobart mixing bowl. The liquid blend is added to the Hobart mixing bowl containing the nicotine blend, binder material, and polydextrose powder, wherein the ingredients are admixed in Hobart mixer (Model N-50) for about 4-5 minutes at about 120 rpm to form a nicotinic compound-containing composition. The nicotinic compound-containing composition is passed through a meat grinder on the Hobart mixer to incorporate the liquid ingredients into the dry ingredients. The nicotinic compound-containing composition is extruded through a grinder apparatus. Upon extrusion, the nicotinic compound-containing composition is placed in a Hobart mixer to form a powder granulation. The mixture of the nicotinic compound-containing composition is about 26 parts binder material, 0.2 parts nicotine, 31.5 parts humectant, 1.2 parts emulsifier, 26 parts polydextrose, 6.2 parts corn syrup, 4.1 parts glycerin, 2 parts salt, 0.2 parts sucralose, and 0.9 parts flavorant.

The nicotinic compound-containing composition is transferred to an injection mold and compressed at about 103,500 kPa for 1 minute. The mold is a stainless steel two-piece block that is filled with the nicotinic compound-containing composition and then compressed via engagement with a hydraulic press unit (Wabach Hydraulic Press, Model 12-102T, Serial 2201). The nicotinic compound-containing composition is removed from the injection mold after cooling at ambient temperature for about 60 minutes.

Other acceptable excipients of injection molded-type formulations are provided, for example, in U.S. patent application Ser. No. 12/957,838 to Cantrell et al., filed Dec. 1, 2010, which is incorporated herein by reference.

Example 5

Preparation of Chewable-type Formulation

A nicotinic compound-containing formulation suitable for use as a chewable component of a pharmaceutical composition for oral use is provided in the following manner. An aqueous mixture is prepared. The aqueous mixture is formed by adding nicotine and hydrating a binder material (gum arabic) with the water. The aqueous mixture is about 49.7 parts binder, about 0.6 parts nicotine, and about 49.7 parts water.

The aqueous mixture is mixed with a salt (NaCl), a buffering agent (sodium hydroxide), a sweetener (sucralose), glycerin, and an emulsifier (sunflower lecithin) and the added components are allowed to dissolve therein. The mixture is heated to about 49° C. The heated mixture is combined with a lipid substance having a melting point of about 38° C. to about 42° C. (available as 108-24-B from AarhusKarlshamn USA Inc.), which has been heated to a melt and flavorant. The mixture of the nicotinic compound-containing composition is about 36 parts aqueous mixture, 24 parts lipid substance, 6 parts glycerin, 0.2 parts emulsifier component, 0.2 parts sucralose, 0.6 parts salt, 0.3 parts buffering agent, 0.6 parts flavorant, and 32 parts water.

The nicotinic compound-containing composition is formed in various ways. In one example, it is deposited into a mold and remains in the mold at ambient conditions until dry and then removed from the mold. In another example, it is poured onto a tabletop to air dry to a semi-moist state and formed into desired shapes using a drop roller.

Example 6

Preparation of Hard Coating-type Formulation

An aqueous mixture is prepared by adding sodium hydroxide, nicotine, and a binder (CMC-15) and the mixture is heated to about 57° C. The aqueous mixture is about 0.3 parts sodium hydroxide, about 2 parts nicotine, about 13 parts CMC-15, and about 84.7 parts water. A mixture of sorbitol, isomalt, maltitol syrup, and sucralose is melted to a liquid, cooled to about 135° C., and added to the aqueous mixture. Flavorant and pigment (to provide a pearlescent appearance) is added to give a nicotinic compound-containing composition that is about 10 parts aqueous mixture (about 0.2 parts nicotine), about 7 parts sorbitol, about 26.2 parts isomalt, about 0.2 parts sucralose, about 8.2 parts maltitol syrup, about 0.2 parts flavorant, and about 48.2 parts water.

The resulting formulation can be cast into sheets (e.g., by casting into sheets on stainless steel plates) or dip- or spray-coated onto the composition described previously in this example. When the formulation is cast into sheets, it can be cut (e.g., with a casting knife) and applied as a sandwiched coating onto the composition described previously in this example. When the formulation is dip- or spray-coated, it is maintained at a temperature of greater than about 66° C., applied as a liquid, and then cooled to harden.

Example 7

Preparation of 2-Layered Products a) Lozenge/Meltable

A lozenge-type formulation is prepared as described in Example 1, poured into molds, and cooled. A meltable-type formulation as described in Example 2 is prepared. However, rather than pouring the flowable slurry into molds, it is applied directly to the surface of the cooled lozenge-type formulation. For example, the molded lozenge-type formulations are dipped into the flowable slurry and it is allowed to dry and harden at room temperature to provide a 2-layered product comprising a lozenge-type core and a meltable-type coating.

b) Lozenge/Chewable

A lozenge-type formulation is prepared as described in Example 1, poured into molds, and cooled. A chewable formulation as described in Example 5 is prepared. The formulation is poured onto a tabletop to air dry to a semi-moist state and formed around the surface of the lozenge-type formulations to provide a 2-layered product comprising a lozenge-type core and a chewable-type coating.

c) Lozenge/Hard Coating

A lozenge-type formulation is prepared as described in Example 1, poured into molds, and cooled. A hard coating-type formulation as described in Example 6 is prepared. The coated formulation is cast into sheets, cut, and applied directly to the surface of the lozenge-type product as a sandwich coating to provide a 2-layered product comprising a lozenge-type core and a hard coating-type coating.

d) Meltable/Lozenge

A meltable-type formulation is prepared as described in Example 2. A lozenge-type formulation as described in Example 1 is prepared, except that rather than pouring the hot mixture into molds, it is applied directly to the surface of the meltable-type formulation. For example, the hot mixture may be introduced into spray coating equipment adapted to maintain a temperature of about 132° C. and sprayed onto the surface of the cooled meltable-type formulation. As noted in Example 1, the mixture must be held at an elevated temperature to maintain sufficient flexibility and pliability to be manipulated into the desired shape. Because the meltable-type formulation may exhibit some degree of melting at such an elevated temperature, steps must be taken to avoid or limit the melting of the meltable-type formulation during the application of the lozenge-type formulation. For example, the meltable-type formulation may be frozen prior to applying the lozenge-type formulation to limit the degree of melting.

e) Meltable/Hard Coating

A meltable-type formulation is prepared as described in Example 2. A hard coating-type formulation as described in Example 6 is prepared. The coated formulation is cast into sheets, cut, and applied directly to the surface of the meltable-type product as a sandwich coating to provide a 2-layered product comprising a meltable-type core and a hard coating-type coating.

f) Starch Molded/Meltable

A starch molded-type formulation is prepared as described in Example 3, poured into molds, and cooled. A meltable-type formulation as described in Example 2 is prepared. However, rather than pouring the flowable slurry into molds, it is applied directly to the surface of the cooled starch molded-type formulation. For example, the starch molded-type formulations are dipped into the flowable slurry and it is allowed to dry and harden at room temperature to provide a 2-layered product comprising a starch molded-type core and a meltable-type coating.

g) Starch Molded/Lozenge

A starch molded-type formulation is prepared as described in Example 3, poured into molds, and cooled. A lozenge-type formulation as described in Example 1 is prepared, except that rather than pouring the hot mixture into molds, it is applied directly to the surface of the starch molded-type formulation. For example, the hot mixture may be introduced into spray coating equipment adapted to maintain a temperature of about 132° C. and sprayed onto the surface of the cooled starch molded-type formulation. As noted in Example 1, the mixture must be held at an elevated temperature to maintain sufficient flexibility and pliability to be manipulated into the desired shape.

h) Injection Molded/Meltable

An injection molded-type formulation is prepared as described in Example 4, injection molded into the desired size and shape, and cooled. A meltable-type formulation as described in Example 2 is prepared. However, rather than pouring the flowable slurry into molds, it is applied directly to the surface of the cooled injection molded-type formulation. For example, the injection molded-type formulations are dipped into the flowable slurry and it is allowed to dry and harden at room temperature to provide a 2-layered product comprising an injection molded-type core and a meltable-type coating.

i) Injection Molded/Lozenge

An injection molded-type formulation is prepared as described in Example 4, injection molded into the desired size and shape, and cooled. A lozenge-type formulation as described in Example 1 is prepared, except that rather than pouring the hot mixture into molds, it is applied directly to the surface of the injection molded-type formulation. For example, the hot mixture may be introduced into spray coating equipment adapted to maintain a temperature of about 132° C. and sprayed onto the surface of the cooled injection molded-type formulation. As noted in Example 1, the mixture must be held at an elevated temperature to maintain sufficient flexibility and pliability to be manipulated into the desired shape.

Example 8

Preparation of 3-Layered Products a) Lozenge/Meltable/Hard Coating

A 2-layered product comprising a lozenge-type core and a meltable-type coating is prepared as described above in Example 7a. A hard coating-type formulation as described in Example 6 is prepared. The coated formulation is cast into sheets, cut, and applied directly to the surface of the 2-layered lozenge/meltable composition as a sandwich coating to provide a 3-layered product comprising a lozenge-type core, a meltable-type first coating and a hard coating-type second coating.

b) Starch Molded/Lozenge/Meltable

A 2-layered product comprising a starch molded-type core and a lozenge-type coating is prepared as described above in Example 7g. A meltable-type formulation as described in Example 2 is prepared. However, rather than pouring the flowable slurry into molds, it is applied directly to the surface of the cooled 2-layered starch molded/lozenge composition. For example, the 2-layered composition is dipped into the flowable slurry and it is allowed to dry and harden at room temperature to provide a 3-layered product comprising a starch molded-type core, a lozenge-type first coating and a meltable-type second coating.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A multi-layered pharmaceutical composition comprising two formulations having different organoleptic properties, wherein the formulations include:
    i) a translucent, dissolvable formulation comprising a sugar substitute in an amount of at least about 80% by weight and a sugar alcohol syrup in an amount of from about 0.1% to about 2% by weight, wherein the sugar substitute is a non-hygroscopic sugar alcohol forming a glassy matrix; and
    ii) a meltable formulation comprising a lipid having a melting point of about 36° C. to about 45° C.
    wherein at least one formulation further comprises one or more nicotinic compounds.

2. The multi-layered pharmaceutical composition of claim 1, wherein the translucent, dissolvable formulation and the meltable formulation each comprise one or more nicotinic compounds.

3. The multi-layered pharmaceutical composition of claim 1, wherein the one or more nicotinic compounds are independently in the form of a free base, a salt, a complex, or a solvate.

4. The multi-layered pharmaceutical composition of claim 3, wherein the one or more nicotinic compounds comprise nicotine polacrilex.

5. The multi-layered pharmaceutical composition of claim 1, wherein the one or more nicotinic compounds comprise a nicotinic compound sorbed onto a porous particulate carrier.

6. The multi-layered pharmaceutical composition of claim 5, wherein the porous particulate carrier comprises microcrystalline cellulose.

7. The multi-layered pharmaceutical composition of claim 1, wherein the form of the pharmaceutical composition is a core formulation surrounded by one or more continuous layers or a core formulation coated by one or more discontinuous layers so as to form a layered or side-by-side configuration of the two or more formulations.

8. The multi-layered pharmaceutical composition of claim 1, wherein the sugar substitute of the translucent, dissolvable formulation comprises isomalt and wherein the sugar alcohol syrup of the translucent, dissolvable formulation comprises maltitol syrup.

9. The multi-layered pharmaceutical composition of claim 1, wherein the translucent, dissolvable formulation comprises a nicotinic compound.

10. The multi-layered pharmaceutical composition of claim 1, wherein the lipid of the meltable formulation has a melting point of about 38° C. to about 41° C.

11. The multi-layered pharmaceutical composition of claim 1, wherein the lipid of the meltable formulation is an animal or plant derived fat, wax, or oil.

12. The multi-layered pharmaceutical composition of claim 1, wherein the meltable formulation comprises a nicotinic compound; the lipid in an amount of from about 10% to about 50% by weight; and further comprises a filler in an amount of from about 20% to about 40% by weight, based on the meltable formulation.

13. The multi-layered pharmaceutical composition of claim 1, wherein the meltable formulation comprises a nicotinic compound; the lipid in an amount of about 30% by weight or greater; and further comprises a filler in an amount of about 30% by weight or greater, based on the meltable formulation.

14. A process for preparing a multi-layered pharmaceutical composition according to claim 1, comprising:
preparing a translucent, dissolvable formulation by combining one or more nicotinic compounds with a sugar substitute and a sugar alcohol syrup to form a first nicotinic compound-containing mixture;
preparing a meltable formulation by combining one or more nicotinic compounds with a lipid component to form a second nicotinic compound-containing mixture;
and either forming the translucent, dissolvable formulation into a desired form and applying the meltable formulation to the translucent, dissolvable formulation, or forming the meltable formulation into a desired form and applying the translucent, dissolvable formulation to the meltable formulation.

15. The process of claim 14, wherein the translucent, dissolvable formulation is formed into a desired form by pouring the first nicotinic compound-containing mixture into a mold.

16. The process of claim 14, wherein the meltable formulation is applied by spray coating, dip coating, or by forming the meltable formulation into a sheet that is applied to the translucent, dissolvable formulation as a sandwiched coating.

17. The process of claim 16, wherein the spray coating or dip coating is conducted at a temperature such that the translucent, dissolvable formulation is maintained in substantially intact form.

18. A method for treating a human subject having a condition, disease, or disorder responsive to stimulation of nicotinic acetylcholinergic receptors, comprising orally administering an effective amount of a multi-layered pharmaceutical composition according to claim 1 to said human subject.

19. The method of claim 18, wherein said administering step comprises administering the multi-layered pharmaceutical composition to a human subject as a smoking cessation aid.

\* \* \* \* \*